US009701985B2

(12) United States Patent
Fisher et al.

(10) Patent No.: US 9,701,985 B2
(45) Date of Patent: Jul. 11, 2017

(54) MDA-9/SYNTENIN PROMOTER TO IMAGE AND TREAT METASTATIC CANCER CELLS

(71) Applicant: Virginia Commonwealth University, Richmond, VA (US)

(72) Inventors: Paul B. Fisher, Richmond, VA (US); Swadesh K. Das, Richmond, VA (US); Mitchell E. Menezes, Richmond, VA (US); Devanand Sarkar, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 14/895,579

(22) PCT Filed: Jun. 4, 2014

(86) PCT No.: PCT/US2014/040898
§ 371 (c)(1),
(2) Date: Dec. 3, 2015

(87) PCT Pub. No.: WO2014/197586
PCT Pub. Date: Dec. 11, 2014

(65) Prior Publication Data
US 2016/0130605 A1    May 12, 2016

Related U.S. Application Data

(60) Provisional application No. 61/830,872, filed on Jun. 4, 2013.

(51) Int. Cl.
| | | |
|---|---|---|
| *C12N 15/00* | (2006.01) | |
| *C12N 15/86* | (2006.01) | |
| *G01N 33/574* | (2006.01) | |
| *A61K 49/00* | (2006.01) | |
| *C07K 14/47* | (2006.01) | |
| *C12N 15/85* | (2006.01) | |
| *G01N 33/50* | (2006.01) | |

(52) U.S. Cl.
CPC .......... *C12N 15/86* (2013.01); *A61K 49/0008* (2013.01); *C07K 14/47* (2013.01); *C12N 15/85* (2013.01); *C12N 15/8509* (2013.01); *G01N 33/5088* (2013.01); *G01N 33/57492* (2013.01); *C12N 2710/10331* (2013.01); *C12N 2710/10345* (2013.01); *C12N 2830/008* (2013.01); *C12N 2830/85* (2013.01)

(58) Field of Classification Search
None
See application file for complete search history.

(56) References Cited

U.S. PATENT DOCUMENTS

| | | | |
|---|---|---|---|
| 4,405,712 A | 9/1983 | Vande Woude et al. | |
| 4,650,764 A | 3/1987 | Temin et al. | |
| 5,175,384 A | 12/1992 | Krimpenfort et al. | |
| 5,252,479 A | 10/1993 | Srivastava | |
| 6,018,097 A | 1/2000 | Selden et al. | |
| 6,080,912 A | 6/2000 | Bremel et al. | |
| 6,262,335 B1 | 7/2001 | Hsiao et al. | |
| 6,451,571 B1 | 9/2002 | Loeb et al. | |
| 6,548,650 B1 | 4/2003 | Fisher | |
| 6,897,024 B2 | 5/2005 | Bussemakers et al. | |
| 6,989,195 B2 | 1/2006 | Anderson | |
| 7,247,297 B2 | 7/2007 | Weichselbaum et al. | |
| 7,321,030 B2 | 1/2008 | Hamada | |
| 7,332,586 B2 | 2/2008 | Franzen et al. | |
| 7,364,727 B2 | 4/2008 | Li et al. | |
| 7,816,131 B2 | 10/2010 | Hung et al. | |
| 8,034,914 B2 | 10/2011 | Hochberg | |
| 8,178,128 B2 | 5/2012 | Golomb et al. | |
| 8,709,466 B2 | 4/2014 | Coady et al. | |
| 8,716,399 B2 | 5/2014 | Wang et al. | |
| 2002/0003791 A1 | 1/2002 | Hayata | |
| 2003/0073205 A1* | 4/2003 | Arslanian ............ | C07D 313/00 435/117 |
| 2006/0179501 A1 | 8/2006 | Chan et al. | |
| 2007/0161031 A1 | 7/2007 | Trinklein et al. | |
| 2008/0213220 A1 | 9/2008 | Fisher et al. | |
| 2009/0311664 A1 | 12/2009 | Fong et al. | |
| 2011/0136221 A1 | 6/2011 | Black | |

(Continued)

FOREIGN PATENT DOCUMENTS

| | | |
|---|---|---|
| WO | WO-89/05345 | 6/1989 |
| WO | WO-90/06997 | 6/1990 |
| WO | WO-92/05266 | 4/1992 |

(Continued)

OTHER PUBLICATIONS

Kimura et al. Genome Res 2006;16:55-65.*
Suzuki et al. Methods Mol Biol 2003;221:73-91.*
Gangemi et al, Plos One Jan. 2012;7 e29989, pp. 1-13.*
Al-Madhoun et al., "Evaluation of Human Thymidine Kinase 1 Substrates as New Candidates for Boron Neutron Capture Therapy," Cancer Res. 64(17): 6280 (2004).
Azab et al., "Enhanced prostate cancer gene transfer and therapy using a novel serotype chimera cancer terminator virus (Ad.5/3-CTV)," J Cell Physiol 229(1): 34-43 (2014).

(Continued)

*Primary Examiner* — Janice Li
(74) *Attorney, Agent, or Firm* — Foley & Lardner LLP

(57) ABSTRACT

Recombinant vectors in which expression of one or more elements (e.g. gene required for viral replication, detectable imaging agents, therapeutic agents, etc.) is driven by an mda-9/syntenin (mda-9) cancer selective promoter are provided, as are cells and transgenic animals that contain such vectors. The vectors are used in cancer therapy and/or diagnostics, especially to visualize (image) and treat metastasis (including in rapid in vitro assays), and the transgenic mice are used to monitor cancer progression and/or the efficacy of candidate therapeutic agents in screening assays.

26 Claims, 6 Drawing Sheets

(56) References Cited

U.S. PATENT DOCUMENTS

2013/0263296 A1 10/2013 Pomper et al.

FOREIGN PATENT DOCUMENTS

| WO | WO-92/07573 | 5/1992 |
| WO | WO-92/14829 | 9/1992 |
| WO | WO-2007/078599 | 7/2007 |
| WO | WO-2012/058522 | 5/2012 |

OTHER PUBLICATIONS

Berkner. "Development of adenovirus vectors for the expression of heterologous genes," Biotechniques 6: 616-626 (1988).
Bhang et al., "Tumor-specific imaging through progression elevated gene-3 promoter-driven gene expression," Nature Med 17: 123-129 (2011).
Blaese et al., "T Lymphocyte-Directed Gene Therapy for ADA-212 SCID: Initial Trial Results After 4 Years," Science 270: 475-479 (1995).
Bonnet et al., "Systemic delivery of DNA or siRNA mediated by linear polyethylenimine (L-PEI) does not induce an inflammatory response," Pharm Res. 25: 2972-2982 (2008).
Boukerche et al., "mda-9/Syntenin promotes metastasis in human melanoma cells by activating c-Src," Proc. Natl. Acad. Sci. USA 105: 15914-15919 (2008).
Boukerche et al., "Mda-9/Syntenin Regulates the Metastatic Phenotype in Human Melanoma Cells by Activating Nuclear Factor-kB," Cancer Res. 67(4): 1812-1822 (2007).
Boukerche et al., "mda-9/Syntenin: a positive regulator of melanoma metastasis," Cancer Res. 65: 10901-10911 (2005).
Boukerche et al., "Src kinase activation is mandatory for MDA-9/syntenin-mediated activation of nuclear factor-kappaB," Oncogene 29: 3054-3066 (2010).
Cai et al., "The improved syntheses of 5-substituted 2'-[18F]fluoro-2'-deoxy-arabinofuranosyluracil derivatives ([18F]FAU, [18F]FEAU, [18F]FFAU, [18F]FCAU, [18F]FBAU and [18F]FIAU) using a multistep one-pot strategy," Nuclear Medicine and Biology 38(5): 659-666 (2011).
Chan et al., "Evaluation of F-18-labeled 5-iodocytidine (18 F-FIAC) as a new potential positron emission tomography probe for herpes simplex virus type 1 thymidine kinase imaging," Nuclear Medicine and Biology 38(7): 987-995 (2011).
Cotten et al., "High-efficiency receptor-mediated delivery of small and large (48 kilobase gene constructs using the endosome-disruption activity of defective or chemically inactivated adenovirus particles," Proc. Natl. Acad. Sci. USA 89(13): 6094-6098 (1992).
Danos et al., "Safe and efficient generation of recombinant retroviruses with amphotropic and ecotropic host ranges," Proc. Natl. Acad. Sci. USA 85(17): 6460-6464 (1988).
Das et al., "Cancer terminator viruses and approaches for enhancing therapeutic outcomes," Adv. Cancer Res. 115:I-38 (2012).
Das et al., "MDA-9/Syntenin and IGFBP-2 Promote Angiogenesis in Human Melanoma," Cancer Res. 73(2): 844-854 (2013).
Das et al., "MDA-9/syntenin: a positive gatekeeper of melanoma metastasis," Frontiers in Bioscience 17: 1-15 (2012).
Dash et al., "Apogossypol derivative BI-97C1 (Sabutoclax) targeting Mcl-1 sensitizes prostate cancer cells to mda-7/IL-24-mediated toxicity." Proc. Natl. Acad. Sci. USA 108: 8785-8790 (2011).
Dash et al., "Developing an effective gene therapy for prostate cancer: new technologies with potential to translate from the laboratory into the clinic," Discov Med 11: 46-56 (2011).
Dash et al., "Enhanced delivery of mda-7/IL-24 using a serotype chimeric adenovirus (Ad.5/3) in combination with the Apogossypol derivative BI-97C1 (Sabutoclax) improves therapeutic efficacy in low CAR colorectal cancer cells." J Cellular Physiol 227: 2145-2153 (2012).
Dash, R. et al., "Enhanced delivery of mda-7/IL-24 using a serotype chimeric adenovirus (Ad.5/3) improves therapeutic efficacy in low CAR prostate cancer cells." Cancer Gene Ther, 2010, vol. 17: 447-456.

Donahue et al., "Reduction in SIV replication in rhesus macaques infused with autologous lymphocytes engineered with antiviral genes," Nature Medicine 4(2):181-186 (1998).
Doronin et al., "Tissue-Specific, Tumor-Selective, Replication-Competent Adenovirus Vector for Cancer Gene Therapy," J. Virol. 75(7): 3314-3324 (2001).
Fisher. "Is mda-7/IL-24 a 'magic bullet' for cancer?" Cancer Res 65: 10128-10138 (2005).
Freireich et al., "Quantitative comparison of toxicity of anticancer agents in mouse, rat, hamster, dog, monkey, and man," Cancer Chemother. Rep. 50(4): 219-44 (1966).
Geller et al., "A Defective HSV-1 Vector Expresses *Eschirichia coli* beta-galactosidase in Cultured Peripheral Neurons," Science 241: 1667-1669 (1988).
Gilad et al., "Artificial reporter gene providing MRI contrast based on proton exchange," Nature Biotechnology 25(2): 217-219 (2007).
Gilad et al., "MRI Reporter Genes," J. Nucl. Med. 49(12): 1905-1908 (2008).
Goldman et al., "Lentiviral Vectors for Gene Therapy of Cystic Fibrosis," Human Gene Therapy 10: 2261-2268 (1997).
Graham et al., "Manipulation of Adenovirus Vectors," Methods in Mol. Biol.: Gene Transfer and Expression Protocols 7: 109-127 (1991).
Greco et al., "Eradication of Therapy-resistant Human Prostate Tumors Using an Ultrasound-guided Site-specific Cancer Terminator Virus Delivery Approach," Mol Ther 18: 295-306 (2010).
Greelish et al., "Stable restoration of the sarcoglycan complex in dystrophic muscle perfused with histamine and a recombinant adeno-associated viral vector," Nature Med. 5:439-443 (1999).
Grootjans et al., "Syntenin, a PDZ protein that binds syndecan cytoplasmic domains," Proc. Natl. Acad. Sci. USA 94: 13683-13688 (1997).
Hallenbeck et al., "A Novel Tumor-Specific Replication-Restricted Adenoviral Vector for Gene Therapy of Hepatocellular Carcinoma," Human Gene Therapy 10(10): 1721-1733 (1999).
Herzog et al., "Long-term correction of canine hemophilia B by gene transfer of blood coagulation factor IX mediated by adeno-associated viral vector," Nature Medicine 5(1): 56-63 (1999).
Ibraheem et al., "Gene therapy and DNA delivery systems," Int J Pharm 459(1-2): 70-83 (2014).
International Preliminary Report on Patentability issued on PCT/US2014/040898, dated Dec. 8, 2015.
Iordanova et al., "In vivo magnetic resonance imaging of ferritin-based reporter visualizes native neuroblast migration," Neuroimage 59(2):1004-1012 (2012).
Jiang, H. et al., "The melanoma differentiation associated gene mda-7 suppresses cancer cell growth." Proc. Natl. Acad. Sci. USA 93(17): 9160-9165 (1996).
Jiang, H. et al., "Use of a sensitive and efficient subtraction hybridization protocol for the identification of genes differentially regulated during the induction of differentiation in human melanoma cells." Mol Cell Different 1: 285-299 (1993).
Kafri et al., "Sustained expression of genes delivered directly into liver and muscle by lentiviral vectors," Nature Genetics 17(3): 314-317 (1997).
Kegelman et al., "MDA-9/syntenin is a key regulator of glioma pathogenesis," Neuro Oncol 16: 50-61 (2014).
Kurihara et al., "Selectivity of a replication-competent adenovirus for human breast carcinoma cells expressing the MUC1 antigen," J. Clin. Invest. 106: 763-771 (2000).
Lee et al., "Selective Activation of Ceruloplasmin Promoter in Ovarian Tumors: Potential Use for Gene Therapy," Cancer Res. 64(5): 1788 (2004).
Li et al., "Assessment of Recombinant Adenoviral Vectors for Hepatic Gene Therapy," Human Gene Therapy 4:403-409 (1993).
Lin et al., "Characterization of a novel melanoma differentiation-associated gene, mda-9, that is down-regulated during terminal cell differentiation," Mol Cell Differ. 4: 317-333 (1996).
Lin et al., "Melanoma differentiation associated gene-9 is a human gamma interferon responsive gene," Gene 207: 105-110 (1998).
Mocarski et al "Viral Vectors." Gluzman and Hughes (eds.). Cold Spring Harbor Laboratory, Cold Spring Harbor, N.U., 1988, pp. 78-84.

(56) References Cited

OTHER PUBLICATIONS

Muller et al., "Synthesis and evaluation of a C-6 alkylated pyrimidine derivative for the in vivo imaging of HSV1-TK gene expression," Nuclear Medicine and Biology 39(2): 235-246 (2012, in press 2011).

Onodera et al., "Development of Improved Adenosine Deaminase Retroviral Vectors," J. Virol. 72(3):1769-1774 (1998).

Piccini et al., "Vaccinia virus as an expression vector," Meth. Enzymology 153: 545-563 (1987).

Qian et al., "Syndecan Binding Protein (SDCBP) Is Overexpressed in Estrogen Receptor Negative Breast Cancers, and Is a Potential Promoter for Tumor Proliferation," PLOS One 8:e60046 (2013).

Rodriguez et al., "Prostate Attenuated Replication Competent Adenovirus (ARCA) CN706: A Selective Cytotoxic for Prostate-specific Antigen-positive Prostate Cancer Cells," Cancer Res. 57(13): 2559-2563 (1997).

Sarkar et al., "Chemoprevention gene therapy (CGT) of pancreatic cancer using perillyl alcohol and a novel chimeric serotype cancer terminator virus," Curr Mol Med. 14(1): 125-140 (2014).

Sarkar et al., "Eradication of therapy-resistant human prostate tumors using a cancer terminator virus," Cancer Res 67: 5434-5442 (2007).

Sarkar et al., "Recent Insights into a Novel Cell Signaling and Metastasis-Associated Gene," Pharmacol Ther. 104: 101-115 (2004).

Sarkar et al., "Targeted virus replication plus immunotherapy eradicates primary and distant pancreatic tumors in nude mice." Cancer Research 65: 9056-9063 (2005).

Sarkar, D. et al. "Dual cancer-specific targeting strategy cures primary and distant breast carcinomas in nude mice." Proc. Natl. Acad. Sci. USA 102: 14034-14039 (2005).

Shackleford et al., "Construction of a clonable, infectious, and tumorigenic mouse mammary tumor virus provirus and a derivative genetic vector," Proc. Natl. Acad. Sci. USA 85: 9655-9659 (1988).

Snyder et al., "Correction of hemophilia B in canine and murine models using recombinant adeno-associated viral vectors," Nature Medicine 5(1): 64-70 (1999).

Su et al., "PEG-3, a nontransforming cancer progression gene, is a positive regulator of cancer aggressiveness and angiogenesis," Proc. Natl. Acad. Sci. USA 96: 15115-15120 (1999).

Su, Z. "Targeting gene expression selectively in cancer cells by using the progression-elevated gene-3 promoter," Proc. Natl. Acad. Sci. USA 102: 1059-1064 (2005).

Venkatesan et., "The potential of celecoxib-loaded hydroxyapatite-chitosan nanocomposite for the treatment of colon cancer," Biomaterials 32(15): 3794-3806 (2011).

Wang et al., "Sustained correction of bleeding disorder in hemophilia B mice by gene therapy," Proc. Natl. Acad. Sci. USA 96: 3906-3910 (1999).

Zabner et al., "Safety and efficacy of repetitive adenovirus-mediated transfer of CFTR cDNA to airway epithelia of primates and cotton rats," Nature Genetics 6:75-83 (1994).

Das et al., "Raf Kinase Inhibitor RKIP Inhibits MDA-9/Syntenin-Mediated Metastasis in Melanoma", Cancer Research, vol. 72, No. 23, Dec. 1, 2012, pp. 6217-6226.

Search Report issued on European Application 14807809.0, mailed Jan. 30, 2017.

\* cited by examiner

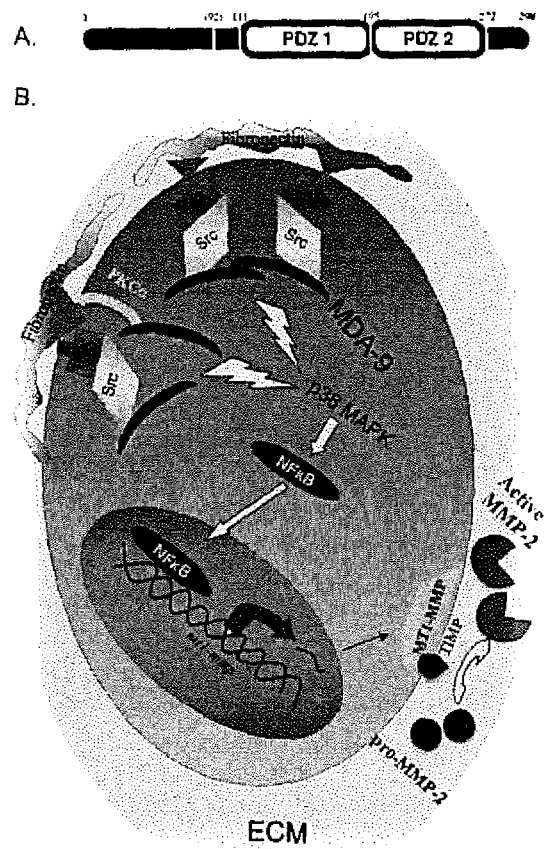
Figure 1 A and B (-1063)
CTTGCTCATGCAAACTTGCTATAATTGCTTTTCATTCTGTTTTTTTAGGCGAGGAGTGTCAATTT
TTTCCGGATTTTCTATGTTAGATAACCATCTCATCTGAAAGCAAAAAGTTTTATTTCTTCCTTCC
CAATCTACCTTGTAATTATTTTTAAATGTCCATTTCATCAGCCTAACTATAACCTTACTGAGAG
CAAAGTTTTCATCTTTAGTTGTCACCTCTTTACACTCAGATTTTTATTAGTTTTGCCATATATT
AAATTATTCTGGCACTAATTTAGCTAGAAATAAACTGCTTGTAAATGCTATTTTGTCAAGGACT
CTACAGTATTCCGTGGTAACTATGATTACTCTTGGGTAAACTGTGCCTCAGTTTCTTTGTCTGT
AATGGGATGTCTTTATAGACTGATGTGAAGACCAAATAAGACTATACATTAAGTTCGTAGAGC
TATGGCTGGCACAAAATCAGCCCTCAAGAAATGATCGTTATGTTTTTTTACTGGGAAGCAATT
ACTTTTGCGCAGCACCACACCTAACTCTCAATAGCGAAGGAATATTAGCTTAGGCGGACAGAG
TAATACGCCCCCCACCCCCAACATCCAAATTTCCAACAGAAAAATAAAGCAGGAGTTGAGAA
GGGGTCGTGAGAGGAACGTTTCTGAGCCTATAGTGGAGAGGTACAGCAAGCGGAGAGTGAGA
CTAGGGCAGCAAGTGGTGGAAGTCGAAGGCATCCCAAGAGGGAACAGGGGCTCCCGAGACCT
CTTTGAATTGGAGGCGACGAGAACCAAGCGACCGTGAGCTGCGATGCACACAGTAGTGAGTG
GGTGGCACGGGGCCCGCGGGCACGAACAGCCGAAGAGCGGAGAAGACTGGGAGCATAACCG
CTGGGCAGCGGGCAGCGGACAGCGGGCGGCATGAACCGCCCCACTTTGCCGGATACCTGGAG
CTGCAGGAACGACCCACACCCAGGCCTCTTTACCCCTACCGCCCCGTTACCTTGGGGACGGGA
TCACCCGACCCGGCGCCGTGCGACTGCGCGGGCTGAAGGCGGGGGCGGTGCCATGACGCGCC
TCGGGGGCGGTCCTCGGGCGCGCACCGCTCTCTTACACTCGGGCCTCAGAAGTCCGTGCCAGT
GACCGGAGGCGGCGGCGGCGAGCGGTTCCTTGTGGGCTAGGTGAGAGGCCAAGGGGGCAAG
GAGGGACGCCGGTGCCAGGTCCCGGGCGCGGGGACTTGGGGCAGAGGTGTGACGGTCCCTGG
GCCACTTCACAGACTGCATCCT (+240)
(SEQ ID NO: 1)

Figure 2A

CTGGAGCTGCAGGAACGACCCACACCCAGGCCTCTTTACCCCTACCGCCCCGTTACCTTGGGG
ACGGGATCACCCGACCCGGCGCCGTGCGACTGCGCGGGCTGAAGGCGGGGGCGGTGCCATGA
CGCGCCTCGGGGGCGGTCCTC (SEQ ID NO: 2)

Figure 2B

A.
B.
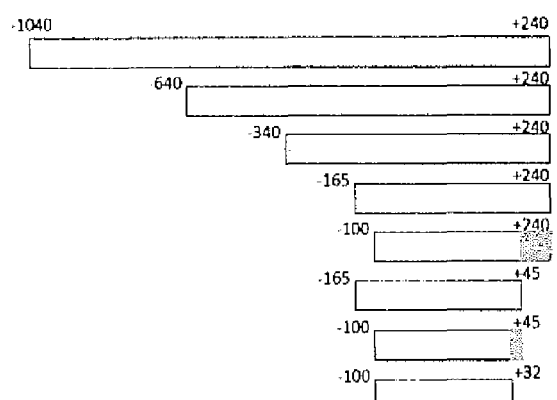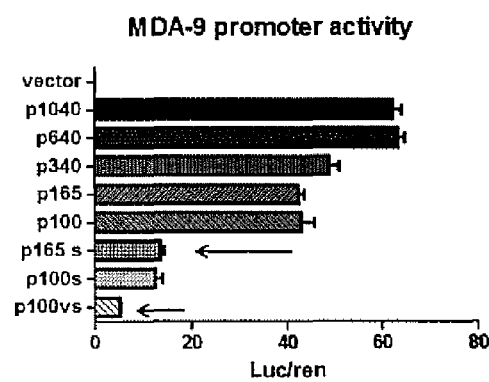
Figure 4A and B

SEQUENCE LISTING

```
<160> NUMBER OF SEQ ID NOS: 2

<210> SEQ ID NO 1
<211> LENGTH: 1280
<212> TYPE: DNA
<213> ORGANISM: Homo sapiens

<400> SEQUENCE: 1
cttgctcatg caaacttgct ataattgctt ttcattctgt tttttaggc gaggagtgtc      60 aattttttcc ggattttcta tgttagataa ccatctcatc tgaaagcaaa aagttttatt    120
tcttccttcc caatctacct tgtaattatt tttaaatgtc catttcatca gcctaactat    180
aaccttactg agagcaaagt tttcatcttt agttgtcacc tcttttacac tcagattttt    240
```

```
attagttttg ccatatatta aattattctg gcactaattt agctagaaat aaactgcttg      300
taaatgctat tttgtcaagg actctacagt attccgtggt aactatgatt actcttgggt      360
aaactgtgcc tcagtttctt tgtctgtaat gggatgtctt tatagactga tgtgaagacc      420
aaataagact atacattaag ttcgtagagc tatggctggc acaaaatcag ccctcaagaa      480
atgatcgtta tgtttttta ctgggaagca attacttttg cgcagcacca cacctaactc       540
tcaatagcga aggaatatta gcttaggcgg acagagtaat acgccccca cccccaacat       600 ccaaatttcc aacagaaaaa taaagcagga gttgagaagg ggtcgtgaga ggaacgtttc      660
tgagcctata gtggagaggt acagcaagcg gagagtgaga ctagggcagc aagtggtgga     720
agtcgaaggc atcccaagag ggaacagggg ctcccgagac ctctttgaat tggaggcgac      780
gagaaccaag cgaccgtgag ctgcgatgca cacagtagtg agtgggtggc acggggcccg     840
cgggcacgaa cagccgaaga gcggagaaga ctgggagcat aaccgctggg cagcgggcag     900
cggacagcgg gcggcatgaa ccgccccact ttgccggata cctggagctg caggaacgac     960
ccacacccag gcctctttac ccctaccgcc ccgttacctt ggggacggga tcacccgacc    1020
cggcgccgtg cgactgcgcg ggctgaaggc ggggcggtg ccatgacgcg cctcggggc      1080 ggtcctcggg cgcgcaccgc tctcttacac tcgggcctca gaagtccgtg ccagtgaccg    1140
gaggcggcgg cggcgagcgg ttccttgtgg gctaggtgag aggccaaggg ggcaaggagg    1200
gacgccggtg ccaggtcccg ggcgcgggga cttggggcag aggtgtgacg gtccctgggc    1260
cacttcacag actgcatcct                                                1280

<210> SEQ ID NO 2
<211> LENGTH: 146
<212> TYPE: DNA
<213> ORGANISM: Artificial Sequence
<220> FEATURE:
<223> OTHER INFORMATION: Synthetic truncated mda-9 promoter

<400> SEQUENCE: 2
ctggagctgc aggaacgacc cacacccagg cctctttacc cctaccgccc cgttaccttg       60
gggacgggat cacccgaccc ggcgccgtgc gactgcgcgg gctgaaggcg ggggcggtgc     120
catgacgcgc ctcgggggcg gtcctc                                          146
```

MDA-9/SYNTENIN PROMOTER TO IMAGE AND TREAT METASTATIC CANCER CELLS

CROSS-REFERENCE TO RELATED APPLICATIONS

This application is a U.S. national stage application under 35 U.S.C. §371 of International Application No. PCT/US2014/040898, filed Jun. 4, 2014, which claims the benefit of U.S. Provisional Application No. 61/830,872, filed Jun. 4, 2013, which are incorporated herein by reference in their entireties.

BACKGROUND OF THE INVENTION

Field of the Invention

The invention generally relates to recombinant vectors for use in cancer therapy and/or diagnostics. In particular, the invention provides vectors in which expression of one or more elements (e.g. genes required for viral replication, detectable imaging agents, therapeutic agents, etc.) is driven by an mda-9/syntenin promoter in a cancer- and/or metastasis-specific manner.

Background of the Invention

Melanoma differentiation associated gene-9/Syntenin (mda-9/syntenin) was originally cloned from metastatic human melanoma cells induced to terminally differentiate by treatment with recombinant human fibroblast interferon plus the protein kinase C activating agent mezerein (Jiang and Fisher, 1993; Lin, et al., 1996, 1998; Sarkar, et al., 2004). Expression of mda-9 is biphasic, with an early peaking (8 to 12 hr) in activity and then a decrease over time (24 to 72 hr). This gene was subsequently cloned as a syndecan interacting protein and named syntenin (Grootjans, et al., 1997). MDA-9/syntenin is a PDL domain containing adapter protein (FIG. 1A) that plays a central role in regulating cell-cell and cell-matrix adhesion. MDA-9/syntenin transduces signals from the cell-surface to the interior through its interaction with a plethora of additional proteins and actively participates in intracellular trafficking, cell-surface targeting, synaptic transmission, and axonal outgrowth (Grootjans, et al., 1997). Recent studies have documented a seminal role of mda-9/syntenin in cancer metastasis (Boukerche, et al., 2008; Das, et al., 2012a, 2013). Overexpression of mda-9/syntenin has been identified in metastatic melanoma, breast and gastric cancer cells in comparison to the primary tumor or poorly metastatic counterparts (Das, et al., 2012a; Qian, et al., 2013). Data available from the website located at cancergenome.nih.gov documents overexpression of mda-9/syntenin in additional cancers such as glioblastoma multiforme, squamous cell carcinoma of the lungs and serous cystadenocarcinoma of the ovary and clear cell carcinoma of the kidneys. Other studies also identify overexpression of mda-9/syntenin in human Hepatocellular Carcinoma (HCC) compared to the normal liver, in bladder cancer vs. normal bladder and in glioblastoma multiforme (GBM) vs. normal brain (Dasgupta, et al., 2013; Kegelman et al., 2014). Forced overexpression of mda-9/syntenin results in increased migration of non-metastatic cancer cells which correlates with a more polarized distribution of F-actin and increased pseudopodia formation. MDA-9/syntenin promotes invasion and metastasis through interactions with c-Src and promotes the formation of an active FAK/c-Src signaling complex leading to NF-κB and matrix metalloproteinase (MMP) activation (Boukerche, et al., 2010) (FIG. 1B). Additionally overexpression of mda-9/syntenin leads to activation of Ras, Rho, Rac, PI3K/Akt and MAPK signaling.

Adaptor molecules, which contain protein-protein interaction domains, are involved in the assembly of multimeric complexes that play an essential role in modulating signal transduction from the extracellular environment to the intracellular milieu by virtue of their association with key regulatory molecules (Das, et al., 2012a). PDZ domains (an acronym for three proteins, postsynaptic density protein PSD95/SAP90, drosophila tumor suppressor DLGA, and tight junction protein ZO-1 containing proteins) are present in a diverse group of over 150 proteins that control a plethora of physiologic processes. MDA-9/syntenin has two PDZ domains: PDZ-1 (a.a.110-193) and PDZ-2 (a.a.194-274) (FIG. 1A). Both PDZ domains are critically involved in metastasis, since deletion mutants (either one of the two PDZ domains) of MDA-9/syntenin significantly reduced lung metastases of melanoma cells compared with the cells transfected with wild type MDA-9/syntenin. The interaction of c-Src with MDA-9/syntenin is mediated by carboxylate-binding loop of PDZ-2 (Boukerche, et al., 2010). However, PDZ-1 also plays a critical role in binding by promoting the proper folding of PDZ-2 that assembles MDA-9/syntenin into a multimeric complex resulting in a more stable functional unit. MDA-9/syntenin through its interaction with itself and with c-Src enables c-Src/FAK signaling complexes clustered at high concentrations on the plasma membrane to amplify signaling through FAK intermolecular autophosphorylation. These events lead to enhanced cell motility, invasion, and metastasis as confirmed by overexpression and knockdown studies (Boukerche, et al., 2005; Boukerche, et al., 2010). Additionally, MDA-9/syntenin can directly regulate new blood vessel formation, angiogenesis (Das, et al., 2013).

Cancer (malignant neoplasia) is a broad group of diseases involving unregulated cell growth. In cancer, cells divide and grow uncontrollably, forming malignant tumors, which may invade nearby parts of the body. The cancer may also spread to more distant parts of the body through the lymphatic system or bloodstream (metastasis). Cancer is usually treated with one or a combination of chemotherapy, radiation therapy and surgery. While treatment methods have advanced significantly, the outcomes for particular cancers is still not optimal, current treatments often have very harsh side effects, and if the cancer is not detected early, the chances of survival are greatly reduced. Metastatic cancer is particularly difficult to locate and treat.

Cancer can be detected in a number of ways, including the presence of certain signs and symptoms, various screening tests, and/or medical imaging. While detection methods have also improved markedly over the years, there is still a need in the art to detect and treat cancers earlier and more effectively. In particular, there is a great need to develop targeted therapeutic and imaging methodology so that e.g. tumors and metastatic cancer cells can be located and eliminated with a minimum of damage to healthy tissue. To that end, it would be advantageous to have available additional cancer-selective and/or cancer-specific promoters in order to develop improved therapeutic and diagnostic constructs for use in the detection and treatment of cancers.

SUMMARY OF THE INVENTION

The melanoma differentiation associated gene-9 (mda-9)/syntenin promoter displays enhanced expression in tumorigenic and metastatic tumor cells of diverse origin. Experiments described herein demonstrate that one level of regulation of expression of mda-9/syntenin is through its promoter. As described herein, this promoter and trucated versions hereof have been isolated and can be used in a variety of cancer-combating scenarios, e.g. to image tumorigenic and metastatic human cancers by linkage to a gene encoding an imaging agent; and/or to drive expression of one or more therapeutic genes, such as mda-7/IL-24 or IFN-gamma. Further, combined therapeutic and imaging constructs are provided which comprise both at least one gene encoding an imaging agent and at least one gene encoding a therapeutic agent, the expression of at least one of which is driven by the mda-9/syntenin promoter. Such constructs provide a way of both imaging and treating cancer, especially metastatic cancers, with a single administered agent, and may be referred to herein as "MetaTheranostics".

Details of these and other features and advantages of the present invention are set forth in the description of invention that follows, and in part will be apparent from the description or may be learned by practice of the invention. The invention will be realized and attained by the compositions and methods particularly pointed out in the written description and claims hereof.

It is an object of this invention to provide cancer cells comprising a recombinant mda-9 cancer selective promoter having a nucleotide sequence that comprises the sequence set forth in SEQ ID NO: 2. In some aspects, the recombinant mda-9 cancer selective promoter has a nucleotide sequence as set forth in SEQ ID NO: 1.

The invention also provides recombinant vectors comprising a recombinant mda-9 cancer selective promoter having a nucleotide sequence that comprises the sequence set forth in SEQ ID NO: 2. In some aspects, the recombinant mda-9 cancer selective promoter is operably linked to at least one gene of interest (e.g. a first gene of interest); and may further include at least one promoter that is not recombinant mda-9 and that is also operably linked to at least one gene of interest (e.g. a second gene of interest, usually different from the gene of interest linked to the mda-9 promoter. The recombinant vector may be a viral vector such as an adenoviral vector, a lentiviral vector, a herpes simplex virus, a measles virus, or a vaccinia virus. The recombinant vector may be present in a nanoparticle carrier, e.g. a nanoparticle carrier comprising polyethyleneimine (PEI). The at least one gene of interest (first, second, and others, e.g. third, fourth, etc. if present in the construct) generally encodes one or more of an anticancer agent, an imaging agent and at least one gene that is required for viral replication. In some aspects, the recombinant vector is present in a transgenic mouse. In some aspects, the recombinant mda-9 cancer selective promoter in the vector has a nucleotide sequence that comprises the sequence set forth in SEQ ID NO: 1.

Cells, which may be cancer cells, comprising any of the recombinant vectors described herein are also provided The invention also provides transgenic mice comprising a transgene under operational control of a cancer selective mda-9 promoter. The cancer selective mda-9 promoter may comprise a nucleotide sequence as set forth in SEQ ID NO: 2, and the transgene may encode a detectable imaging agent. The transgenic mouse may be prone to developing cancer and/or metastatic cancer (e.g. by the presence of another transgene or a genetic mutation).

The invention also provides methods of non-invasively imaging cancer cells and metastases in a transgenic mouse that develops cancer, comprising i) providing a transgenic mouse by genetically engineering a mouse to contain and express a detectable imaging agent under operational control of a cancer selective mda-9 promoter; ii) providing at least one compound transgenic mouse by breeding the transgenic mouse provided in step i) to a mouse that is genetically prone to develop cancer; and iii) non-invasively imaging cancer cells in said at least one compound transgenic mouse by detecting expression of said detectable imaging agent in cancer cells of said at least one compound transgenic mouse. In some aspects, the method further comprises the steps of: if cancer cells are detected in said detecting step, administering a candidate anti-cancer agent to said compound transgenic mouse; then repeating said step of detecting cancer cells; and, if no or fewer cancer cells are detected in said repeating step than in said detecting step, then, concluding that said candidate anti-cancer agent is an effective anti-cancer agent. However, if the same number or more cancer cells are detected, then one would conclude that the candidate anti-cancer agent is not an effective anti-cancer agent. The method may further comprise the steps of: if cancer cells are not detected in said transgenic mouse, administering a candidate anti-cancer cancer agent to said compound transgenic mouse; repeating said step of detecting cancer cells after a time period during which said transgenic mouse would develop cancer; and, if no cancer cells are detected in said repeating step or if fewer cancer cells are detected in said repeating step than would be predicted in the absence of said candidate anti-cancer cancer agent, then, concluding that said candidate anti-cancer agent is an effective cancer prevention agent. In any of these methods, the cancer selective mda-9 promoter may be one that comprises a nucleotide sequence as set forth in SEQ ID NO: 2.

The invention also provides methods of treating and/or preventing and/or imaging cancer and/or metastatic cancer in a patient in need thereof, comprising administering to the patient a composition comprising a recombinant vector as described herein. The type of cancer may be, for example, melanoma, brain cancer, breast cancer, liver cancer, esophageal cancer, cervical cancer, lung cancer, colon cancer, bladder cancer, uterine cancer, endometrial cancer, gastric cancer, pancreatic cancer, prostate cancer, neuroblastoma, sarcoma, or thyroid cancer. The cancer may be metastatic cancer.

The invention also provides in vitro methods for detecting cancerous and pre-cancerous cells in a biological sample from a patient, comprising: exposing cells in said biological sample to a recombinant construct comprising a recombinant mda-9 cancer selective promoter operably linked to a reporter gene that produces a detectable signal when expressed, and measuring the detectable signal in cells of said biological sample. In some aspects, the mda-9 cancer selective promoter that is used in the assay has a nucleotide sequence that comprises the sequence set forth in SEQ ID NO: 2. In some aspects, the biological sample is blood. In yet other aspects, the recombinant construct is a nanoparticle, e.g. a nanoparticle comprising polyethyleneimine (PEI). The invention also provides kits for carrying out the assay methods.

BRIEF DESCRIPTION OF THE DRAWINGS

FIGS. 1A and B. Model of MDA-9/syntenin-augmented invasion and metastasis. A. Schematic representation showing MDA-9/Syntenin domain organization. B. Upon engagement with extracellular matrix (fibronectin), MDA-9/syntenin physically interacts with c-Src in a highly cooperative manner, with the PDZ2 being the dominant motif and then interacting with PDZ1 resulting in the assembly of MDA-9/syntenin into multimeric complexes and consequently a more stable functional unit. Fibronectin stimulation also increases the association of PKCa and MDA-9/syntenin in the plasma membrane and activates c-Src/FAK complex.

FIG. 2A-D. A, Nucleotide sequence of full length mda-9/syntenin promoter (SEQ ID NO: 1); B, minimal truncated promoter region (SEQ ID NO: 2); C, potential transcription factor binding sites; numbering of residues is in reference to numbering in FIG. 2A.

FIGS. 4A and B. 5' and 5' plus 3' deletions of the mda-9 promoter were generated and the luciferase activity was assessed in breast cancer cells. A, deletions; B, promoter activity. Numbering is with reference to the sequence in FIG. 2A.

DETAILED DESCRIPTION

The mda-9/syntenin gene is a pro-metastatic gene SDCBP (encoding syndecan-binding protein-1, "syntenin-1", "MDA-9") is upregulated in a majority of human cancers. Studies using gain and loss of function indicate that altering expression of this gene affects metastasis in vivo and regulates tumor angiogenesis, either enhancing (gain of function) or inhibiting (loss of function) metastasis and angiogenesis. The promoter region of this gene, mda-9-Prom, has now been isolated and characterized. The promoter advantageously displays elevated expression in cancer cells, including metastatic cancer cells. Having multiple promoters available that can distinguish normal from tumorigenic and metastatic cells is advantageous for developing novel therapeutics, including, for example, bipartite and tripartite therapeutic and diagnostic viruses as described herein.

Accordingly, constructs, vectors and transgenic mice comprising at least one gene, the expression of which is under operational control of the mda-9-Prom, (which may be referred to herein as the mda-9 promoter or the mda-9/syntenin promoter or mda-9-Prom) are provided herein, as are methods of using each of these aspects of the invention. This promoter, and active variants thereof, is/are used to selectively drive expression of genes of interest in cancer cells, especially metastatic cancer cells, in a variety of scenarios (e.g. diagnostics, therapeutics and combinations thereof, as described in detail below). Transgenic mice comprising the promoter are also encompassed.

MDA-9 Promoter and Functional Variants Thereof

Figure 2C:
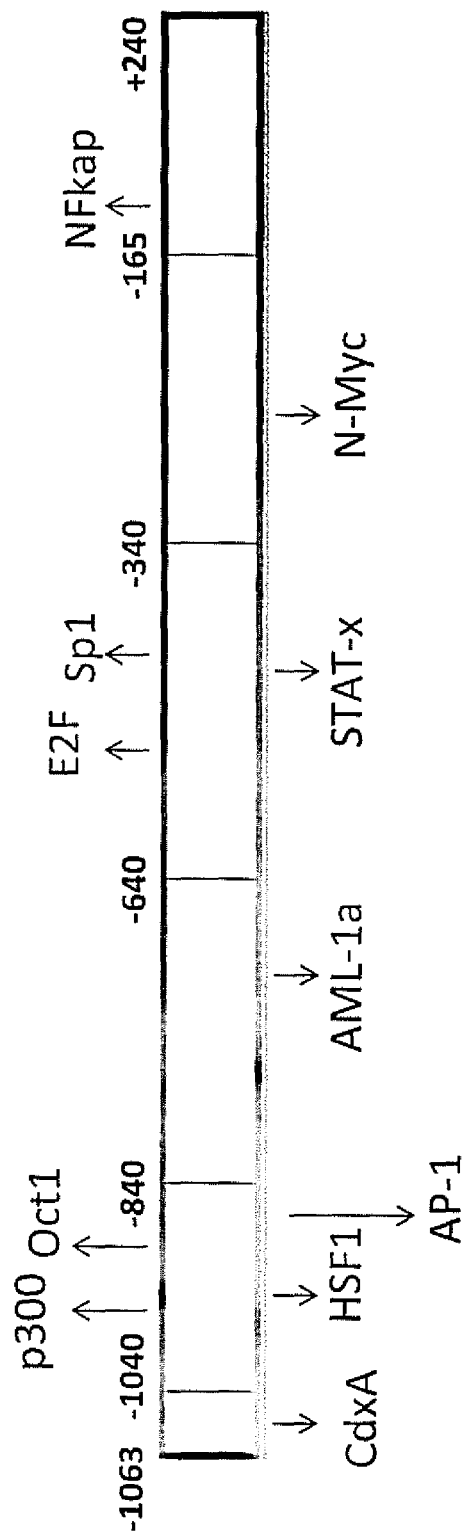

The nucleotide sequence of mda-9 promoter is presented in FIG. 2 as SEQ ID NO: 1. However, as shown herein, truncated versions of mda-9 promoter also exhibit promoter activity, with an exemplary minimum promoter sequence being SEQ ID NO: 2 (FIG. 2; nucleotides −100 to +45 with reference to SEQ ID NO: 1; shaded residues in FIG. 2A). As used herein "mda-9 promoter" refers to a nucleotide sequence that functions as a promoter when operably linked to a gene of interest, and which contains, at a minimum, the nucleotide sequence represented by SEQ ID NO: 2. The mda-9 promoter sequence may be SEQ ID NO: 2, or may contain the nts of SEQ ID NO: 2 plus other either 3' and/or 5' flanking sequences. The flanking sequences may be those found in nature (e.g. the full length promoter as in SEQ ID NO: 1, in which case the promoter is generally located within a construct and has at least one additional heterologous, non-native sequence at its 3' and/or 5' ends. Non-natural truncated promoter sequences of intermediate length (length between that of SEQ ID NO: 1 and SEQ ID NO: 2) are also encompassed, including those represented in e.g. FIG. 4A and FIG. 5. Such truncated sequences may include, in addition to the −100 to +45 nucleotide region of SEQ ID NO: 1, which is SEQ ID NO: 2, regions that extend from e.g. about −1000, −950, −900, −850, −800, −750, −700, −650, −600, −550, −500, −450, −400, −350, −300, −250, −200, −150, −100, or −50, or 0 (including all integer values in between these exemplary values), to about 0, +10, +20, +30, +40, +50, +60, +70, +80, +90, +100, +110, +120, +130, +140, +150, +160, +170, +180, +190, +200, +210, +220, +230, or +240 (including all integer values in between these exemplary values). In particular, sequences ranging from about −100, −95, −90, −85, −80, −75, −70, −65, −60, −55, −50, −45, −40, −35, −30, −35, −20, −15, −10, −5 and 0 (including all integer values in between these exemplary values) and 0, +5, +10, +15, +20, +25, +30, +35, +40 and +45 (including all integer values in between these exemplary values).

The invention further provides various sequences having at least about 50, 55, 60, 65, 70, 76, 80, 85, 90, 95, 96, 97, 98, 99% identity to the mda-9 promoters described herein, so long as the nucleotide substitutions in such variant sequences do not impair the function/activity of the promoter, or at least as long as at least about 50, 55, 60, 65, 70, 76, 80, 85, 90, 95 or 100% of the activity is retained. In some aspects, the activity of a variant may exceed that of the mda-9 promoters described herein.

In addition to substitutions, various deletions and/or additions of nucleotides may be tolerated, or even advantageous, e.g. deletions of from about 1-100 nucleotides (e.g. about 1, 5, 10, 15, 20, 25, 30, 35, 40, 45, 50, 55, 60, 65, 70, 75, 80, 85, 90 or 95 nucleotides) or insertions of about 1-100 nucleotides (e.g. about 1, 5, 10, 15, 20, 25, 30, 35, 40, 45, 50, 55, 60, 65, 70, 75, 80, 85, 90 or 95 nucleotides), throughout the sequence are encompassed, so long as promoter activity is not impaired but is within the ranges listed above. Deletions and insertions may be internal or at the 3' or 5' ends (or both) of the sequence. "Insertions" may result in what is essentially a full-length mda-9 promoter, or a recombinant promoter that is intermediate in length between full-length mda-9 and truncated mda-9 (tmda-9) as described herein, or a promoter that is shorter than the tmda-9 promoter that is disclosed herein, having e.g. at least about 200, 500, 550, 600, 650, 700, 750 or 800 basepairs.

Vectors and Other Constructs and/or Carriers

Herein, the terms "construct" and "vector" refer to a recombinant nucleic acid that contains at least one mda-9 promoter, usually operably linked to a nucleotide sequence that encodes a product of interest, which may be a protein or polypeptide, with which the promoter is not linked in nature. However, nanoparticles containing such nucleic acids may also be included within this meaning, as may liposomes and other types of vehicles, which contain or house or are used to deliver nucleic acids. Constructs and vectors are generally made or manufactured using genetic engineering or other laboratory techniques. The terms may be used interchangeable herein.

Vectors which may be used in the practice of the invention include both viral and non-viral vectors. Exemplary non-viral vectors that may be employed include but are not limited to, for example: cosmids or plasmids; and, particularly for cloning large nucleic acid molecules, bacterial artificial chromosome vectors (BACs) and yeast artificial chromosome vectors (YACs); as well as liposomes (including targeted liposomes); cationic polymers; ligand-conjugated lipoplexes; polymer-DNA complexes; poly-L-lysine-molossin-DNA complexes; chitosan-DNA nanoparticles; polyethylenimine (PEI, e.g. branched PET)-DNA complexes; various nanoparticles and/or nanoshells such as multifunctional nanoparticles, metallic nanoparticles or shells (e.g. positively, negatively or neutral charged gold particles, cadmium selenide, etc.); ultrasound-mediated microbubble delivery systems; various dendrimers (e.g. polyphenylene and poly(amidoamine)-based dendrimers; etc.

In addition, viral vectors may be employed. Exemplary viral vectors include but are not limited to: bacteriophages, various baculoviruses, retroviruses, adenoviruses, lentiviruses, and the like. Those of skill in the art are familiar with viral vectors that are used in "gene therapy" applications, which include but are not limited to: Herpes simplex virus vectors (Geller et al., Science, 241:1667-1669 (1988)); vaccinia virus vectors (Piccini et al., Meth. Enzymology, 153: 545-563 (1987)); cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., Proc. Natl. Acad. Sci. USA, 85:6460-6464 (1988); Blaese et al., Science, 270:475-479 (1995); Onodera et al., J. Virol., 72:1769-1774 (1998)); adenovirus vectors (Berkner, Biotechniques, 6:616-626 (1988); Cotten et al., Proc. Natl. Acad. Sci. USA, 89:6094-6098 (1992); Graham et al., Meth. Mol. Biol., 7:109-127 (1991); Li et al., Human Gene Therapy, 4:403-409 (1993); Zabner et al., Nature Genetics, 6:75-83 (1994)); adeno-associated virus vectors (Goldman et al., Human Gene Therapy, 10:2261-2268 (1997); Greelish et al., Nature Med., 5:439-443 (1999); Wang et al., Proc. Natl. Acad. Sci. USA, 96:3906-3910 (1999); Snyder et al., Nature Med., 5:64-70 (1999); Herzog et al., Nature Med., 5:56-63 (1999)); retrovirus vectors (Donahue et al., Nature Med., 4:181-186 (1998); Shackleford et al., Proc. Natl. Acad. Sci. USA, 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., Nature Genetics, 17:314-317 (1997), as well as viruses that are replication-competent conditional to a cancer cell such as oncolytic herpes virus NV 1066 and vaccinia virus GLV-1h68, as described in United States patent application 2009/0311664. In particular, adenoviral vectors may be used, e.g. targeted viral vectors such as those described in published United States patent application 2008/0213220.

Those of skill in the art will recognize that the choice of a particular vector will depend on the details of its intended use. Typically, one would not use a vector that integrates into the host cell genome due to the risk of insertional mutagenesis, and would design vectors so as to avoid or minimize the occurrence of recombination within a vector's nucleic acid sequence or between vectors.

Host cells which contain the recombinant mda-9 promoter or vectors containing the promoter are also encompassed, e.g., in vitro cells such as cultured cells, or bacterial or insect cells which are used to store, generate or manipulate the vectors, and the like. The constructs and vectors may be produced using known recombinant technology or by synthetic (e.g. chemical) means.

In one aspect, therapeutic conditionally replication competent adenoviruses are developed in which the E1A/E1B genes are regulated in a cancer- and metastasis-specific manner, e.g. by the mda-9 promoter. By combining cancer- and/or metastases-specific or selective expression with expression of a second gene (e.g. within the same construct), such as mda-7/IL-24 or interferon-gamma, usually under control of a different promoter, Metastasis Terminator Viruses (MTVc) can be generated for enhanced cancer therapy.

In another aspect, nanoparticle approaches for systemic imaging of metastases are developed. The nanoparticles include mda-9-Prom linked to a gene of interest, for example, to HSV-Tk or another gene for imaging in humans, and/or to a therapeutic gene. The nanoparticles may also include and/or one or more promoters (in addition to mda-9) that are operationally linked to one or more additional genes of interest. The promoters and genes may be on the same strand of nucleic acid or may be on separate strands. Several nanoparticulate drug delivery systems are known in the art and any suitable system may be utilized. For example, those described in U.S. Pat. Nos. 6,989,195; 7,332,586, 8,709,466; 8,716,399; and others. Exemplary types of nanoparticles that may be employed include but are not limited to: various block co-polymers that form micells, carbon-based nanostructures, hydrophilic carbonic clusters functionalized with polyethylene glycol or PEG-HCC; albumin nanoparticles e.g. in liposomes, nanoparticles made of polyethylene glycol (PEG), various biodegradable nanoparticles, "Minicell" nanoparticle built from the membranes of mutant bacteria; LeukoLike Vectors' or LLVs which are drug-carrying silicon nanoparticles coated with lipoprotein, various nanostructured lipid nanocarrier-based system (NLCS), nanoparticles of polylactic-coglycolic acid, nanodiamonds and nanodiamond clusters, silica based nanoparticles, shell-core nanoparticle with a liposomal core and a gel like shell of cross-linked hyaluronic acid (HA), gold nanoparticles, silica-based nanoparticle chips, liposomes, exosomes, nanodiamonds, polyphosphazenes, dendrimers, polyplex (L-PEI, poly(propyleneimine) (PPI), poly-l-lysine (PLL), poly-ϵ-caprolactone coated with poly-l-lysine (PLL-PCL), Poly (amidoamine) (PAMAM), poly(isoprene-block-dimethyl-aminoethyl methacrylate) (PI-b-PDMAEMA), b-PEI), lipoplex (e.g. (N-[1-(2,3-dioleyloxy)propyl]-N,N,N-trimethylammonium chloride (DOTMA) and N-[1-(2,3-dioleoyloxy)propyl]-N,N,N-trimethylammonium chloride (DOTAP)) (±)-N-(2-hydroxyethyl)-N,N-dimethyl-2,3-bis (tetradecyloxy)-1-propanaminium bromide/dioleoylphosphatidylethanolamine (DMRIE/DOPE), DC-Chol, Lipid 67, DOGS, (sperminecarboxamido)ethyl]-N,N-dimethyl-1-propanaminium trifluoroacetate (DOSPA), olymeric nanoconjugates, High-density lipoprotein (HDL), gels (chitosan and gelatin), block copolymer micelles, inversion emulsions, etc. Also encompassed are various lipid-based systems such as cationic lipids—lipoplexes, lipid-modified polycations, emulsions, HDL; nanoparticles: polyplexes, micelles (block and graft copolymers), nanogels; inorganic nanoparticles: calcium phosphate particles, Superparamagnetic iron oxide nanoparticles (SPIONS), nanodiamonds; natural vesicles; Virus like particles (VLPs), exosomes, and the like, as well as composites thereof e.g. Au plus PPI, and radioactive variants. See Ibraheem et al, Int J Pharm 459 (2014) 70-83 and U.S. Pat. No. 8,178,128.

In one aspect, the nanoparticle is formed from or includes polyethyleneimine (PEI), and a DNA construct of the invention is attached to the PEI molecules.

To that end, the present disclosure describes exemplary vectors such as adenoviral vectors (which may be referred to herein as "Cancer Terminator Viruses" or "CTVs" (Sarkar, et al., 2007; Sarkar, et al., 2005a; Das et al., 2012b), which replicate selectively in cancer cells. In some aspects, the CTVs simultaneously produce a therapeutic cytokine (for example, mda-7/IL-24) and/or genes necessary for adenoviral replication using the mda-9 promoter and one additional promoter. In one type of non-limiting, exemplary "bipartite" adenovirus, the E1A/E1B genes of adenovirus are under transcriptional regulation of the mda-9 promoter and expression of the anti-cancer agent mda-7/IL-24 is controlled by a different promoter, e.g., the non-selective constitutive CMV promoter This type of construct shows selective activity in inducing toxicity (apoptosis) uniquely in cancer cells, and especially in metastatic cancer cells. While vectors and constructs which contain two or more mda-9-Proms each driving expression of a gene or other element of interest are also encompassed. However, to avoid recombination, generally only one mda-9 promoter is used per construct, together with one or more additional cancer-specific (e.g. PEG-Prom) or cancer-selective (e.g. hTERT) promoters. In an exemplary "tripartite" virus three promoters (mda-9 promoter, PEG-Prom and CMV-Prom) are utilized. The PEG-Prom displays cancer-specific expression (Su, et al., 1999; Su et al., 2005; Bhang, et al., 2011).

Promoters that may be Used with the MDA-9 Promoter in Constructs

The constructs and vectors described herein contain at least one copy of an mda-9 promoter that is operably linked to a gene of interest. "Operably linked" refers to the promoter being located or positioned within a recombinant construct so as to interact with a nucleotide sequence encoding a gene of interest in a manner that results in successful transcription of the nucleic acid.

However, the constructs may also include one or more other promoters that are operably linked to other genes of interest. Depending on the overall design, the additional promoters may or may not be specific or selective for driving expression within cancer cells, and may be inducible or constitutive. Exemplary suitable cancer selective/specific promoters (and or promoter/enhancer sequences) that may be used include but are not limited to: CCN1 promoter, tCCN1 promoter, PEG-PROM (e.g. as described in U.S. patent application Ser. No. 13/881,777), astrocyte elevated gene 1 (AEG-1) promoter, survivin-Prom, human telomerase reverse transcriptase (hTERD-Prom, hypoxia-inducible promoter (HIF-1-α), DNA damage inducible promoters (e.g. GADD promoters), metastasis-associated promoters (metalloproteinase, collagenase, etc.), ceruloplasmin promoter (Lee et al., Cancer Res Mar. 1, 2004 64; 1788), mucin-1 promoters such as DF3/MUC1 (see U.S. Pat. No. 7,247,297), HexII promoter as described in US patent application 2001/00111128; prostate-specific antigen enhancer/promoter (Rodriguez et al. Cancer Res., 57: 2559-2563, 1997); α-fetoprotein gene promoter (Hallenbeck et al. Hum. Gene Ther., 10: 1721-1733, 1999); the surfactant protein B gene promoter (Doronin et al. J. Virol., 75: 3314-3324, 2001); MUC1 promoter (Kurihara et al. Clin. Investig., 106: 763-771, 2000); H19 promoter as per U.S. Pat. No. 8,034, 914; those described in issued U.S. Pat. Nos. 7,816,131, 6,897,024, 7,321,030, 7,364,727, and others; etc., as well as derivative forms thereof. Any promoter that is specific or selective for driving gene expression in cancer cells, or in cells of a particular type of cancer (so as to treat e.g. prostate, colon, breast, etc. primary and metastatic cancer) may be used in the practice of the invention. By "specific for driving gene expression in cancer cells" we mean that the promoter, when operably linked to a gene, functions to promote transcription of the gene only when located within a cancerous, malignant cell, but not when located within normal, non-cancerous cells. By "selective for driving gene expression in cancer cells" we mean that the promoter, when operably linked to a gene, functions to promote transcription of the gene to a greater degree when located within a cancer cell, than when located within non-cancerous cells. For example, the promoter drives gene expression of the gene at least about 2-fold, or about 3-, 4-, 5-, 6-, 7-, 8-, 9-, or 10-fold, or even about 20-, 30-, 40-, 50-, 60-, 70-, 80-, 90- or 100-fold or more (e.g. 500- or 1000-fold) when located within a cancerous cell than when located within a non-cancerous cell, when measured using standard gene expression measuring techniques that are known to those of skill in the art.

Additional promoters (including tissue- or cell-selective and/or specific and non-selective/non-specific promoters include but are not limited to: neuroendocrine cell-specific and neuroendocrine cell-preferential promoters, SIRT1, IRF6, SV40 IE, RSV LTR, GAPDH, ubiquitin, bovine papilloma virus or polyoma, RIP1, multimerized RIP and HIP promoters (e.g. CMV), murine molony leukemia virus (MMLV-LTR), mouse tumor virus, avian sarcoma viruses, adenovirus II promoters, e.g. the Ad2 major late promoter (Ad2 MLP), tyrosinase promoter, melanoma inhibitory activity (MIA), melanocortin 1 receptor (receptor MC1R, cyclooxygenase 2 (Cox-2), CXCR4, and BIRC5 SV40 and CMV promoters melanoma-specific promoter Tyrex2 chimeric promoter CMV-hTERT a chimeric double promoter based on promoters of the hASH1 and EZH2 genes, etc.

The transcriptional elements may include other transcription or translation supporting elements such as enhancers, etc. and the promoters may be heterologous (not associated with the encoded gene of interest in nature) or homologous (associated with the encoded gene of interest in nature).

The transcriptional elements may include other transcription or translation supporting elements such as enhancers, regulatory elements, response elements, etc. and the promoters may be heterologous (not associated with the encoded gene of interest in nature) or homologous (associated with the encoded gene of interest in nature).

Exemplary Genes and Elements of Interest that may be Expressed Using MDA-9 Promoter Alone or in Combination with Other Promoters A variety of molecules may be expressed under control of an mda-9 promoter and/or under control of other promoters that are used in combination with mda-9 promoter. In some aspects, a gene encoding a therapeutic molecule, e.g., a protein or polypeptide, which is deleterious to cancer cells is operably linked to a cancer-specific or selective promoter as described herein. The therapeutic protein may kill cancer cells (e.g., by initiating or causing apoptosis or toxic autophagy), or may slow their rate of growth (e.g., may slow their rate of proliferation), or may arrest their growth and development or otherwise damage the cancer cells in some manner, or may even render the cancer cells more sensitive to other anti-cancer agents, etc.

Genes encoding therapeutic molecules that may be employed as described herein include but are not limited to suicide genes, including genes encoding various enzymes; oncogenes; tumor suppressor genes; toxins; cytokines; oncostatins; TRAIL, etc. Exemplary enzymes include, for example, thymidine kinase (TK) and various derivatives thereof; TNF-related apoptosis-inducing ligand (TRAIL), xanthine-guanine phosphoribosyltransferase (GPT); cytosine deaminase (CD); hypoxanthine phosphoribosyl transferase (HPRT); etc. Exemplary tumor suppressor genes include p53, Retinoblastoma tumor suppressor gene (Rb), Wilm's Tumor Gene Product, Phosphotyrosine Phosphatase (PTPase), AdE1A and nm23. Suitable toxins include Pseudomonas exotoxin A and S; diphtheria toxin (DT); *E. coli* LT toxins, Shiga toxin, Shiga-like toxins (SLT-1, -2), ricin, abrin, supporin, gelonin, etc. Suitable cytokines include interferons and interleukins such as interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations thereof. Other anti-tumor agents include: GM-CSF interleukins, tumor necrosis factor (TNF); interferon-beta and virus-induced human Mx proteins; TNF alpha and TNF beta; human melanoma differentiation-associated gene-7 (mda-7), also known as interleukin-24 (IL-24), various truncated versions of mda-7/IL-24 such as M4, and specific splice variants of mda-7/IL-24; siRNAs and shRNAs targeting important growth regulating or oncogenes which are required by or overexpressed in cancer cells; antibodies such as antibodies that are specific or selective for attacking cancer cells; etc.

When the therapeutic agent is TK (e.g. viral TK), a TK substrate such as acyclovir; ganciclovir; various thymidine analogs (e.g. those containing o-carboranylalkyl groups at the 3-position [Cancer Res Sep. 1, 2004 64; 6280]) is administered to the subject. These drugs act as prodrugs, which in themselves are not toxic, but are converted to toxic drugs by phosphorylation by viral TK. Both the TK gene and substrate must be used concurrently to be toxic to the host cancer cell.

Exemplary Applications of the MDA-9 Promoter

The mda-9 promoter displays elevated cancer-selective activity in a variety of human cancers, with minimal activity in normal cells. The mda-9 promoter may be used to express anticancer agents and/or to express imaging agents, especially in constructs, which contain at least one other gene of interest whose expression is driven by at least one promoter that is not mda-9. In some aspects, the construct is a "bi-partite" construct comprising 2 different promoters, one of which is mda-9. In other aspects, the construct is "tripartite" comprising 3 different promoters, one of which is mda-9.

In particular, due to its cancer selectivity, the mda-9 promoter can be used to treat or image tumors and metastases. Exemplary imaging genes include HSV-tk and other in vivo imaging genes encoding agents that can be used in humans, which could be administered as a nanoparticle using PEI (Bonnet, et al., 2008; Bhang et al., 2011) or another suitable carrier for administration, which is generally systemic.

Therapy and Administration

Targeted cancer therapy is carried out by administering the constructs, vectors, etc. which encode one or more copies of a recombinant vector containing an mda-9 promoter as described herein to a patient in need thereof. The vector compositions (preparations) of the present invention are typically administered systemically, although this need not always be the case, as localized administration (e.g. intratumoral, or into an external orifice such as the vagina, the nasopharygeal region, the mouth; or into an internal cavity such as the thoracic cavity, the cranial cavity, the abdominal cavity, the spinal cavity, etc.) is not excluded. For systemic distribution of the vector, the preferred routes of administration include but are not limited to: intravenous, by injection, transdermal, via inhalation or intranasally, or via injection or intravenous administration of a cationic polymer-injection based vehicle (e.g. vivo-jetPEI™). Liposomal delivery, which when combined with targeting moieties will permit enhanced delivery. The ultrasound-targeted microbubble-destruction technique (UTMD) may also be used to deliver imaging and theranostic agents (Dash et al. Proc Natl Acad Sci USA. 2011 May 24; 108 (21):8785-90. Epub 2011 May 9]; hydroxyapatite-chitosan nanocomposites (Venkatesan et al. Biomaterials. 2011 May; 32(15):3794-806); and others (Dash et al. Discov Med. 2011 January; 11(56):46-56; review); etc. Any method that is known to those of skill in the art, and which is commensurate with the type of construct that is employed, may be utilized.

Those of skill in the art will recognize that the amount of a construct or vector that is administered will vary from patient to patient, and possibly from administration to administration for the same patient, depending on a variety of factors, including but not limited to: weight, age, gender, overall state of health, the particular disease being treated, and other factors, and that the amount and frequency of administration is best established by a health care professional such as a physician or oncologist. Typically, optimal or effective tumor-inhibiting or tumor-killing amounts are established e.g. during animal trials and during standard clinical trials. Those of skill in the art are familiar with conversion of doses e.g. from a mouse to a human, which is generally done through body surface area, as described by Freireich et al. (Cancer Chemother Rep 1966; 50(4):219-244); and see Tables 1 and 2 below, which are taken from the website located at dtp.nci.nih.gov.

TABLE 1

Conversion factors in mg/kg

| | Mouse wt. 20 g | Rat wt 150 g | Monkey wt 3 kg | Dog wt 8 kg | Human wt 60 kg |
|---|---|---|---|---|---|
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | 1⅔ | 1 | ½ |
| Man | 12 | 7 | 3 | 2 | 1 |

For example, given a dose of 50 mg/kg in the mouse, an appropriate dose in a monkey would be 50 mg/kg×¼=13 mg/kg; or a dose of about 1.2 mg/kg is about 0.1 mg/kg for a human.

TABLE 2

Representative Surface Area to Weight Ratios

| Species | Body Weight (kg) | Surface Area (sq. m.) | Km factor |
|---|---|---|---|
| Mouse | 0.02 | 0.0066 | 3.0 |
| Rat | 0.15 | 0.025 | 5.9 |
| Monkey | 3.0 | 0.24 | 12 |
| Dog | 8.0 | 0.4 | 20 |
| Human, child | 20 | 0.8 | 25 |
| Human, adult | 60 | 1.6 | 37 |

To express the dose as the equivalent mg/sq. m. dose, multiply the dose by the appropriate factor. In adult humans, 100 mg/kg is equivalent to 100 mg/kg×37 kg/sq. m.=3700 mg/sq. m.

In general, for treatment methods, the amount of a vector such as a plasmid will be in the range of from about 0.01 to about 5 mg/kg or from about 0.05 to about 1 mg/kg (e.g. about 0.1 mg/kg), and from about $10^5$ to about $10^{20}$ infectious units (IUs), or from about $10^8$ to about $10^{13}$ IUs for a viral-based vector. In general, for therapy plus imaging methods, the amount of a vector will be in the range of from about 0.01 to about 5 mg/kg or from about 0.05 to about 1 mg/kg (e.g. about 0.1 mg/kg) of e.g. a plasmid, and from about $10^5$ to about $10^{20}$ infectious units (IUs), or from about $10^8$ to about $10^{13}$ IUs for a viral-based vector. Those of skill in the art are familiar with calculating or determining the level of an imaging signal that is required for adequate detection. For example, for radiopharmaceuticals such as [$^{124}$]FIAU, an injection on the order or from about 1 mCi to about 10 mCi, and usually about 5 mCi, (i.e. about 1 mg of material) is generally sufficient.

Further, one type of vector or more than one type of vector may be administered in a single administration, e.g. a therapy vector plus an imaging vector, or two (or more) different therapy vectors (e.g. each of which have differing modes of action so as to optimize or improve treatment outcomes), or two or more different imaging vectors, etc.

Typically cancer treatment requires repeated administrations of the compositions. For example, administration may be daily or every few days, (e.g. every 2, 3, 4, 5, or 6 days), or weekly, bi-weekly, or every 3-4 weeks, or monthly, or any combination of these, or alternating patterns of these. For example, a "round" of treatment (e.g. administration once a week for a month) may be followed by a period of no administration for a month, and then followed by a second round of weekly administration for a month, and so on, for any suitable period of time, as required to optimally treat the patient.

In addition, the compositions may be administered in conjunction with other treatment modalities known in the art, such as various chemotherapeutic agents such as Pt drugs and other chemotherapy agents, radiation therapy, substances that boost the immune system, antibiotic agents, and the like; and/or with detection and imaging methods (e.g. in conjunction with mammograms, X-rays, Pap smears, prostate specific antigen (PSA) tests, etc.

The subjects or patients to whom the compositions of the invention are administered are typically mammals, frequently humans, but this need not always be the case. Veterinary applications are also contemplated.

Systemic virotherapy delivery can be hampered for several reasons including: 1) trapping of viruses in the liver; 2) clearance of viruses by the immune system; 3) lack of true cancer-specific expression of transgenes; and 4) when using adenoviruses, the lack of sufficient Coxsackie Adenovirus Receptors (CAR) to permit viral entry into certain cancer cells. These problems are overcome with novel bipartite and tripartite viruses described herein combined with the ultrasound-targeted microbubble destruction (UTMD) approach (Greco et al., 2010; Dash et al., 2011a; Dash et al. 2011b) and/or by producing chimeric viruses in the Ad.5/3 backbone (Azab et al., 2012, 2014; Sarkar et al., 2014) which are less likely to undergo trapping, clearance, and which are more readily able to enter cancer cells. A systemic administration approach is thus possible for both diagnostic and theranostics, ("MetaTheranostics").

Imaging Plus Treatment

In some embodiments, the invention provides cancer treatment protocols in which treating the disease, e.g. killing, destroying, or otherwise damaging the cancer cells, is combined with imaging of cancer cells and tumors. These protocols may be referred to herein as "theranostics" or "combined therapies" or "combination protocols", or by similar terms and phrases.

In some aspects, the combined therapy involves administering to a cancer patient a vector that encodes, in a single construct, both at least one recombinant vector containing a mda-9 promoter and at least one additional promoter, one of which drives expression of a therapeutic molecule and the other of which drives expression of a reporter gene (for imaging). In addition, one or more genes that are otherwise necessary for the vector or construct to perform its function may be expressed, e.g. by yet another promoter, or in tandem with the mda-9 promoter or the additional promoter. In this embodiment, expression of one or more of the genes is generally mediated by a cancer cell specific or selective promoter such as mda-9. Preferably, at least two different promoters are used in this embodiment in order to prevent or lessen the chance of crossover and recombination within the construct. Alternatively, tandem translation mechanisms may be employed, for example, the insertion of one or more internal ribosomal entry site (IRES) into the construct, which permits translation of multiple mRNA transcripts from a single mRNA. In this manner, both a reporter protein/polypeptide and a therapeutic protein/polypeptide that is lethal or toxic to cancer cells, and, optionally vector-related genes (such as adenoviral structural genes) are selectively or specifically produced within the targeted cancer cells.

Alternatively, the polypeptides encoded by the constructs of the invention (e.g. plasmids) may be genetically engineered to contain a contiguous sequence comprising a reporter and a therapeutic gene, e.g. separated by with an intervening sequence that is cleavable within the cancer cell, e.g. a sequence that is enzymatically cleaved by intracellular proteases, or even that is susceptible to non-enzymatic hydrolytic cleavage mechanisms. In this case, cleavage of the intervening sequence results in production of functional polypeptides, i.e. polypeptides which are able to carry out their intended function, e.g. they are at least 50, 60, 70, 80, 90, or 100% (or possible more) as active as the protein sequences on which they are modeled or from which they are derived, when measured using standard techniques that are known to those of skill in the art.

In other aspects of combined imaging and therapy, two different vectors may be administered, one of which is an "imaging vector or construct" as described herein, and the other of which is a "therapeutic vector or construct" as described herein. At least one of the vectors comprises an mda-9 promoter.

In other aspects of combined imaging and therapy, the genes of interest are encoded in the genome of a viral vector that is capable of transcription and/or translation of multiple mRNAs and/or the polypeptides or proteins they encode, by virtue of the properties inherent in the virus. In this embodiment, such viral vectors are genetically engineered to contain and express genes of interest (e.g., both a reporter gene and at least one therapeutic gene) under the principle control of one or more cancer specific promoters, at least one of which is an mda-9 promoter.

In the "therapy plus imaging" aspect of the invention, the vectors/constructs include at least one transcribable element that is either directly detectable using imaging technology, or which functions with one or more additional molecules in a manner that creates a signal that is detectable using imaging technology. The transcribable element is operably linked to a promoter, which may be a cancer selective/specific promoter as described above, and is generally referred to as a "reporter" molecule. Reporter molecules can cause production of a detectable signal in any of several ways: they may encode a protein or polypeptide that has the property of being detectable in its own right; they may encode a protein or polypeptide that interacts with a second substance and causes the second substance to be detectable; they may encode a protein or polypeptide that sequesters a detectable substance, thereby increasing its local concentration sufficiently to render the surrounding environment (e.g. a cancer cell) detectable. If the gene product of the reporter gene interacts with another substance to generate a detectable signal, the other substance is referred to herein as a "complement" of the reporter molecule.

Examples of reporter proteins or polypeptides that are detectable in their own right (directly detectable) include those which exhibit a detectable property when exposed to, for example, a particular wavelength or range of wavelengths of energy. Examples of this category of detectable proteins include but are not limited to: green fluorescent protein (GFP) and variants thereof, including mutants such as blue, cyan, and yellow fluorescent proteins; proteins which are engineered to emit in the near-infrared regions of the spectrum; proteins which are engineered to emit in the short-, mid-, long-, and far-infrared regions of the spectrum; etc. Those of skill in the art will recognize that such detectable proteins may or may not be suitable for use in humans, depending on the toxicity or immunogenicity of the reagents involved. However, this embodiment has applications in, for example, laboratory or research endeavors involving animals, cell culture, tissue culture, various ex vivo procedures, etc.

Another class of reporter proteins is those, which function with a complement molecule. In this embodiment, a construct comprising a gene encoding a reporter molecule is administered systemically to a subject in need of imaging, and a molecule that is a complement of the reporter is also administered systemically to the subject, before, after or together with the construct. If administered prior to or after administration of the construct, administration of the two may be timed so that the diffusion of each entity into cells, including the targeted cancer cells, occurs in a manner that results in sufficient concentrations of each within cancer cells to produce a detectable signal, e.g. typically within about 1 hour or less. if the two are administered "together", then separate compositions may be administered at the same or nearly the same time (e.g. within about 30, 20, 15, 10, or 5 minutes or less), or a single composition comprising both the construct and the complement may be administered. In any case, no interaction between the reporter and the complement can occur outside of cancer cells, because the reporter is not produced and hence does not exist in any other location, since its transcription is controlled by a cancer specific/selective promoter.

One example of this is the oxidative enzyme luciferase and various modified forms thereof, the complement of which is luciferin. Briefly, catalysis of the oxidation of its complement, luciferin, by luciferase produces readily detectable amounts of light. Those of skill in the art will recognize that this system is not generally used in humans due to the need to administer the complement, luciferin to the subject. However, this embodiment is appropriate for use in animals, and in research endeavors involving cell culture, tissue culture, and various ex vivo procedures.

Another exemplary protein of this type is thymidine kinase (TK), e.g. TK from herpes simplex virus 1 (HSV 1), or from other sources. TK is a phosphotransferase enzyme (a kinase) that catalyzes the addition of a phosphate group from ATP to thymidine, thereby activating the thymidine for incorporation into nucleic acids, e.g. DNA. Various analogs of thymidine are also accepted as substrates by TK, and radiolabeled forms of thymidine or thymidine analogs may be used as the complement molecule to reporter protein TK. Without being bound by theory, it is believed that once phosphorylated by TK, the radiolabeled nucleotides are retained intracellularly because of the negatively charged phosphate group; or, alternatively, they may be incorporated into e.g. DNA in the cancer cell, and thus accumulate within the cancer cell. Either way, they provide a signal that is readily detectable and distinguishable from background radioactivity. Also, the substrate that is bound to TK at the time of imaging provides an additional signal in the cancer cell. In fact, mutant TKs with very low Kms for substrates may augment this effect by capturing the substrate. The radioactivity emitted by the nucleotides is detectable using a variety of techniques, as described herein. This aspect of the use of TK harnesses the labeling potential of this enzyme; the toxic capabilities of TK are described below.

Various TK enzymes or modified or mutant forms thereof may be used in the practice of the invention, including but not limited to: HSV1-TK, HSV1-sr39TK, mutants with increased or decreased affinities for various substrates, temperature sensitive TK mutants, codon-optimized TK, the mutants described in U.S. Pat. No. 6,451,571 and US patent application 2011/0136221, both of which are herein incorporated by reference; various suitable human TKs and mutant human TKs, etc.

Detectable TK substrates that may be used include but are not limited to: thymidine analogs such as: "fialuridine" i.e. [1-(2-deoxy-2-fluoro-1-D-arabinofuranosyl)-5-iodouracil], also known as "FIAU" and various forms thereof, e.g. 2'-fluoro-2'-deoxy-β-D-5-[$^{125}$I] iodouracil-arabinofuranoside ([$^{125}$I] FIAU), [$^{124}$I]FIAU; thymidine analogs containing o-carboranylalkyl groups at the 3-position, as described by Al Mahoud et al., (Cancer Res Sep. 1, 2004 64; 6280), which may have a dual function in that they mediate cytotoxicity as well, as described below; hydroxymethyl] butyl)guanine (HBG) derivatives such as 9-(4-$^{18}$F-fluoro-3-[hydroxymethyl] butyl)guanine ($^{18}$F-FHBG); 2'-deoxy-2'-[$^{18}$F]-fluoro-1-beta-D-arabinofuranosyl-5-iodouracil($^{18}$F-FEAU), 2'-deoxy-2'-[$^{18}$F]-fluoro-5-methyl-1-β-L-arabinofuranosyluracil ($^{18}$F-FMAU),1-(2'-deoxy-2'-fluoro-beta-D-arabinofuranosyl)-5-[$^{18}$F] iodouracil ($^{18}$F-FIAU), 2'-deoxy-2'-[$^{18}$F]-fluoro-1-beta-D-arabinofuranosyl-5-iodouracil ($^{18}$F-FIAC, see, for example, Chan et al., Nuclear Medicine and Biology 38 (2011) 987-995; and Cal et al., Nuclear Medicine and Biology 38 (2011) 659-666); various alkylated pyrimidine derivatives such as a C-6 alkylated pyrimidine derivative described by Muller et al. (Nuclear Medicine and Biology, 2011, in press); and others.

Other exemplary reporter molecules may retain or cause retention of a detectably labeled complement by any of a variety of mechanisms. For example, the reporter molecule may bind to the complement very strongly (e.g. irreversibly) and thus increase the local concentration of the complement within cancer cells; or the reporter molecule may modify the complement in a manner that makes egress of the complement from the cell difficult, or at least slow enough to result in a net detectable accumulation of complement within the cell; or the reporter may render the complement suitable for participation in one or more reactions which "trap" or secure the complement, or a modified form thereof that still includes the detectable label, within the cell, as is the case with the TK example presented above.

One example of such a system would be an enzyme-substrate complex, in which the reporter is usually the enzyme and the complement is usually the substrate, although this need not always be the case: the reporter may encode a polypeptide or peptide that is a substrate for an enzyme that functions as the "complement". In some embodiments, the substrate is labeled with a detectable label (e.g. a radio-, fluorescent-, phosphoresent-, colorimetric-, light emitting-, or other label) and accumulates within cancer cells due to, for example, an irreversible binding reaction with the enzyme (i.e. it is a suicide substrate), or because it is released from the enzyme at a rate that is slow enough to result in a detectable accumulation within cancer cells, or the reaction with the enzyme causes a change in the properties of the substrate so that it cannot readily leave the cell, or leaves the cell very slowly (e.g. due to an increase in size, or a change in charge, hydrophobicity or hydrophilicity, etc.); or because, as a result of interaction or association with the enzyme, the substrate is modified and then engages in subsequent reactions which cause it (together with its detectable tag or label) to be retained in the cells, etc.

Other proteins that may function as reporter molecules in the practice of the invention are transporter molecules which are located on the cell surface or which are transmembrane proteins, e.g. ion pumps which transport various ions across cell membranes and into cells. An exemplary ion pump is the sodium-iodide symporter (NIS) also known as solute carrier family 5, member 5 (SLC5A5). In nature, this ion pump actively transports iodide (I$^-$) across e.g. the basolateral membrane into thyroid epithelial cells. Recombinant forms of the transporter encoded by sequences of the constructs described herein may be selectively transcribed in cancer cells, and transport radiolabeled iodine into the cancer cells. Other examples of this family of transporters that may be used in the practice of the invention include but are not limited to norepinephrine transporter (NET); dopamine receptor; various estrogen receptor systems, ephrin proteins such as membrane-anchored ephrin-A (EFNA) and the transmembrane protein ephrin-B (EFNB); epidermal growth factor receptors (EGFRs); insulin-like growth factor receptors (e.g. IGF-1, IGF-2), etc.; transforming growth factor (TGF) receptors such as TGFα; etc. In these cases, the protein or a functional modified form thereof is expressed by the vector of the invention and the ligand molecule is administered to the patient. Usually, the ligand is labeled with a detectable label as described herein, or becomes detectable upon association or interaction with the transporter. In some embodiments, detection may require the association of a third entity with the ligand, e.g. a metal ion. The ligand may also be a protein, polypeptide or peptide.

In addition, antibodies may be utilized in the practice of the invention. For example, the vectors of the invention may be designed to express proteins, polypeptides, or peptides which are antigens or which comprise antigenic epitopes for which specific antibodies have been or can be produced. Exemplary antigens include but are not limited to tumor specific proteins that have an abnormal structure due to mutation (protooncogenes, tumor suppressors, the abnormal products of ras and p53 genes, etc.); various tumor-associated antigens such as proteins that are normally produced in very low quantities but whose production is dramatically increased in tumor cells (e.g. the enzyme tyrosinase, which is elevated in melanoma cells); various oncofetal antigens (e.g. alphafetoprotein (AFP) and carcinoembryonic antigen (CEA); abnormal proteins produced by cells infected with oncoviruses, e.g. EBV and HPV; various cell surface glycolipids and glycoproteins which have abnormal structures in tumor cells; etc. The antibodies, which may be monoclonal or polyclonal, are labeled with a detectable label and are administered to the patient after or together with the vector. The antibodies encounter and react with the expressed antigens or epitopes, which are produced only (or at least predominantly) in cancer cells, thereby labeling the cancer cells. Conversely, the antibody may be produced by the vector of the invention, and a labeled antigen may be administered to the patient. In this embodiment, an antibody or a fragment thereof, e.g., a Fab (fragment, antigen binding) segment, or others that are known to those of skill in the art, are employed. In this embodiment, the antigen or a substance containing antigens or epitopes for which the antibody is specific is labeled and administered to the subject being imaged.

Other examples of such systems include various ligand binding systems such as reporter proteins/polypeptides that bind ligands which can be imaged, examples of which include but are not limited to: proteins (e.g. metalloenzymes) that bind or chelate metals with a detectable signal; ferritin-based iron storage proteins such as that which is described by Ordanova and Ahrnes (NeuroImage, 2011, in press); and others. Such systems of reporter and complement may be used in the practice of the invention, provided that the reporter or the complement can be transcribed under control of a cancer promoter, and that the other binding partner is detectable or can be detectably labeled, is administrable to a subject, and is capable of diffusion into cancer cells. Those of skill in the art will recognize that some such systems are suitable for use e.g. in human subjects, while other are not due to, for example, toxicity. However, systems in the latter category may be well-suited for use in laboratory settings.

In yet other aspects, the cancer-specific or cancer-selective promoters in the vectors of the invention drive expression of a secreted protein that is not normally found in the circulation. In this embodiment, the presence of the protein may be detected by standard (even commercially available) methods with high sensitivity in serum or urine. In other words, the cancer cells that are detected are detected in a body fluid.

In yet other aspects, the cancer-specific or cancer-selective promoters in the vectors of the invention drive transcription of a protein or antigen to be expressed on the cell surface, which can then be tagged with a suitable detectable antibody or other affinity reagent. Candidate proteins for secretion and cell surface expression include but are not limited to: β-subunit of human chorionic gonadotropin (β hCG); human α-fetoprotein (AFP), and streptavidin (SA).

β hCG is expressed in pregnant women and promotes the maintenance of the corpus luteum during the beginning of pregnancy. The level of β hCG in non-pregnant normal women and men is 0-5 mIU/mL. hCG is secreted into the serum and urine and β hCG has been used for pregnancy test since the β-subunit of hCG is shared with other hormones. Urine β hCG can be easily detected by a chromatographic immunoassay (i.e. pregnancy test strip, detection threshold is 20-100 mIU/mL) at home-, physician's office- and laboratory-based settings. The serum level can be measured by chemiluminescent or fluorescent immunoassays using 2-4 mL of venous blood for more quantitative detection. β hCG has been shown to be secreted into the media when it was expressed in monkey cells. Human AFP is an oncofetal antigen that is expressed only during fetal development and in adults with certain types of cancers. AFP in adults can be found in hepatocellular carcinoma, testicular tumors and metastatic liver cancer. AFP can be detected in serum, plasma, or whole blood by chromatographic immunoassay and by enzyme immunoassay for the quantitative measurement.

Strepavadin (SA) can also be used as a cell surface target in the practice of the invention. The unusually high affinity of SA with biotin provides very efficient and powerful target for imaging and therapy. To bring SA to the plasma membrane of the cancer cells, SA can be fused to glycosylphosphatidylinositol (GPI)-anchored signal of human CD14.

GPI-anchoring of SA will be suitable for therapeutic applications since GPI-anchor proteins can be endocytosed to the recycling endosomes. Once expressed on the cell surface, SA can then be bound by avidin conjugates that contain a toxic or radiotoxic warhead. Toxic proteins and venoms such as ricin, abrin, Pseudomonas exotoxin (PE, such as PE37, PE38, and PE40), diphtheria toxin (DT), saporin, restrictocin, cholera toxin, gelonin, Shigella toxin, and pokeweed antiviral protein, *Bordetella pertussis* adenylate cyclase toxin, or modified toxins thereof, or other toxic agents that directly or indirectly inhibit cell growth or kill cells may be linked to avidin; as could toxic low molecular weight species, such as doxorubicin or taxol or radionuclides such as $^{125}$I, $^{131}$I, $^{111}$In, $^{177}$Lu, $^{211}$At, $^{225}$Ac, $^{213}$Bi and $^{90}$Y; antiangiogenic agents such as thalidomide, angiostatin, antisense molecules, COX-2 inhibitors, integrin antagonists, endostatin, thrombospondin-1, and interferon alpha, vitaxin, celecoxib, rofecoxib; as well as chemotherapeutic agents such as: pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast. growth factor (FGF) inhibitors); angiotensin receptor blacker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers; caspase activators; and chromatin disruptors, especially those which can be conjugated to nanoparticles The detectable components of the system (usually a complement or substrate) may be labeled with any of a variety of detectable labels, examples of which are described above. In addition, especially useful detectable labels are those which are highly sensitive and can be detected non-invasively, such as the isotopes $^{124}$I, $^{123}$I, $^{99}$mTc, $^{18}$F, $^{86}$Y, $^{11}$C, $^{125}$I, $^{64}$Cu, $^{67}$Ga, $^{68}$Ga, $^{201}$Tl, $^{76}$Br, $^{75}$Br, $^{111}$In, $^{82}$Rb, $^{13}$N, and others.

Those of skill in the art will recognize that many different detection techniques exist which may be employed in the practice of the present invention, and that the selection of one particular technique over another generally depends on the type of signal that is produced and also the medium in which the signal is being detected, e.g. in the human body, in a laboratory animal, in cell or tissue culture, ex vivo, etc. For example, bioluminescence imaging (BLI); fluorescence imaging; magnetic resonance imaging [MRI, e.g. using lysine rich protein (LRp) as described by Gilad et al., Nature Biotechnology, 25, 2 (2007); or creatine kinase, tyrosinase, β-galactosidase, iron-based reporter genes such as transferring, ferritin, and MagA; low-density lipoprotein receptor-related protein (LRP; polypeptides such as poly-L-lysine, poly-L-arginine and poly-L-threonine; and others as described, e.g. by Gilad et al., J. Nucl. Med. 2008; 49(12); 1905-1908); computed tomography (CT); positron emission tomography (PET); single-photon emission computed tomography (SPECT); boron neutron capture; for metals: synchrotron X-ray fluorescence (SXRF) microscopy, secondary ion mass spectrometry (SIMS), and laser ablation inductively coupled plasma mass spectrometry (LA-ICP-MS) for imaging metals; photothermal imaging (using for example, magneto-plasmonic nanoparticles, etc.

For aspects of the invention, which encompass both treatment and imaging, the administration protocols may be any which serve the best interest of the patient. For example, initially, an imaging vector alone may be administered in order to determine whether or not the subject does indeed have cancer, or to identify the locations of cancer cells in a patient that has already been diagnosed with cancer. If cancer is indeed indicated, then compositions with therapeutic vectors are administered as needed to treat the disease. Usually a plurality of administrations is required as discussed above, and one or more, and sometimes all of these, include at least one imaging vector together with a least one therapeutic vector; or optionally, a single vector with both capabilities. The ability to alternate between therapy and imaging, or to concomitantly carry out both, is a distinct boon for the field of cancer treatment. This methodology allows a medical professional to monitor the progress of treatment in a tightly controlled manner, and to adjust and/or modify the therapy as necessary for the benefit of the patient. For example, administration of a therapeutic and an imaging vector may be alternated; or, during early stages of treatment, initially an imaging vector may be administered, followed by therapy and imaging vectors together until the tumors are no longer visible, followed by imaging vector alone for a period of time deemed necessary to rule out or detect recurrence or latent disease.

Compositions

The present invention provides compositions, which comprise one or more vectors or constructs as described herein and a pharmacologically suitable (physiologically acceptable) carrier. The compositions are usually for systemic administration. The preparation of such compositions is known to those of skill in the art. Typically, they are prepared either as liquid solutions or suspensions, or as solid forms suitable for solution in, or suspension in, liquids prior to administration. The preparation may also be emulsified. The active ingredients may be mixed with excipients, which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any of one or more ingredients known in the art to provide the composition in a form suitable for administration. The final amount of vector in the formulations may vary. However, in general, the amount in the formulations will be from about 1-99%.

Types of Cancer that can be Treated and/or Imaged

The constructs and methods of the invention are not specific for any one type of cancer. By "cancer" we mean malignant neoplasms in which cells divide and grow uncontrollably, forming malignant tumors, and invade nearby parts of the body. Cancer may also spread or metastasize to more distant parts of the body through the lymphatic system or bloodstream and the mda-9 promoter is particularly suitable for treatment and imaging of metastatic cancers. The constructs and methods of the invention may be employed to image, diagnose, treat, monitor, etc. any type of cancer, tumor, neoplastic or tumor cells including but not limited to: osteosarcoma, ovarian carcinoma, breast carcinoma, melanoma, hepatocarcinoma, lung cancer, brain cancer, colorectal cancer, hematopoietic cell cancer, prostate cancer, cervical carcinoma, retinoblastoma, esophageal carcinoma, bladder cancer, neuroblastoma, renal cancer, gastric cancer, pancreatic cancer, and others. The mda-9 promoter could also be used when linked to a reporter gene, such as luciferase, for detecting tumor cells in the bloodstream, i.e., circulating tumor cells (CTCs).

In addition, the invention may also be applied to imaging and therapy of benign tumors, which are generally recognized as not invading nearby tissue or metastasizing, for example, moles, uterine fibroids, etc.

Transgenic Animals

This disclosure also provides transgenic non-human eukaryotic animals or other eukaryotic organisms (e.g. insects) whose germ cells and somatic cells contain at least one gene of interest under operational control of the mda-9 promoter, and offspring and cells thereof (whether present in the animal or excised (removed) from the animal). In one aspect, the transgenic animal is a mouse, although transgenic animals of other species are also encompassed, e.g. rats, guinea pigs, pigs, hamsters, rabbits, primates, fish, *Drosophila*, worms, etc.

In one aspect, at least one gene of interest that is under operational control of the mda-9 promoter is a reporter gene as described herein, such as a luciferase gene.

Those of skill in the art are familiar with various methods of generating transgenic non-human animals. See, for example, U.S. Pat. Nos. 6,018,097 and 6,262,335 and US patent applications 20060179501 and 2002003791, the complete contents of each of which are hereby incorporated by reference in entirety. Techniques for creating transgenic non-human animals include but are not limited to, e.g., by microinjection, using retroviral vectors, via embryonic stem cell transfer, etc. (see, for example, U.S. Pat. Nos. 6,080,912 and 5,175,384, the complete contents of which are hereby incorporated by reference in entirety).

In an exemplary procedure, generation and identification of mda-9-luc2 (mda-9-Prom-luc) transgenic mice is accomplished by: microinjecting a suitable mda-9-luc2 construct into male pronucleus of fertilized single-cell mouse embryos obtained from mating CB6F1 (C57BL/6×Balb/C) males and females. The injected embryos are then reimplanted into the oviducts of pseudopregnant CD-1 female mice. Offspring are screened for the mda-9 transgene by PCR analysis of genomic tail DNA using e.g. a β-globin intron 2 sense primer (e.g. 5'-CCCTCTGCTAACCATGTTCATGC-3', SEQ ID NO: 2) and a suitable luc2 antisense primer (e.g. 5'-TCTTGCTCACGAATACGACGGTG-3', SEQ ID NO: 3), and detecting the PCR product.

In some aspects, the transgenic animals are single transgenic animals having a single transgene. Alternatively, the animals may be doubly, triply, etc. transgenic e.g. by insertion of a second, third, etc. expressible transgene, or by cross breeding the animals with another transgenic animal. Generally, the transgenic traits are stably maintained in the animal from generation to generation, e.g. offspring also possess the traits. The genes of interest under control of e.g., the mda-9 promoter may be integrated into the animal's chromosome or may remain as generationally transmissible extra-chromosomal elements. Alternatively, the genes may be transiently expressed in the animal.

In one aspect, the transgenic animal is doubly transgenic for a reporter gene and a gene that causes the development of cancer. The transgenic animals that contain an expressible reporter gene under control of the mda-9 cancer selective promoter may be used for a variety of applications. For example, the progression of cancer, especially metastasis, may be studied using the mice by imaging at various stages of cancer progression and/or under various conditions, e.g. after exposure or administration of various treatment modalities. The animals may be used to define the molecular basis of metastasis initiation and progression and to design and test approaches to inhibit metastasis. The animals may be used to screen candidate therapeutics by administering a candidate therapeutic or combination of therapeutics, and monitoring the progression of the cancer in comparison to control animals who do not receive the treatment, and/or who receive other treatments.

Transgenic animals having only a reporter gene under control of the mda-9 promoter may be used to assess the cancer- and/or metastasis-causing effects of various substances or conditions to which they are exposed, e.g. various suspected carcinogens, various environmental conditions, dietary influences, lifestyle influences (e.g. exercise, stress, etc.); and the like.

For all such screening and testing procedures, typically the results are expressed in suitable measured units, e.g. time until tumor development, tumor volume, metastasis occurrence, tumor shrinkage, etc. and the results are compared to that of one or more suitable control values. The comparison allows a skilled practitioner to conclude whether or not the experimental variable (e.g. the candidate therapeutic, the possible carcinogen, etc.) has exerted an effect that differs from that seen in the suitable, matched control animals. For example, a decrease in the incidence of cancer development, or a decrease in metastasis, or a decrease in tumor volume, would support a conclusion that a candidate therapeutic should be selected as efficacious in preventing or treating cancer, as appropriate. And the development of cancer in response to exposure to a potential carcinogen would indicate that the substance or condition is indeed carcinogenic, while the absence of cancer would warrant the opposite conclusion. In this manner, the efficacy of, for example, small molecule metastasis inhibitors, virotherapies, etc. can be assessed.

Using these methods, so-called "Con View Mouse and Met View Mouse" are developed in which development of primary tumors and/or metastasis and/or angiogenesis is followed noninvasively using in vivo imaging approaches.

In Vitro Assays

The mda-9/syntenin promoter operably linked with a reporter gene as described herein may be used in a rapid in vitro assay to detect circulating tumor cells (CTCs) or cells with metastatic potential. A suitable biological sample is obtained from a patient. In an exemplary aspect, peripheral blood mononucleated cell (PBMCs) and/or other suitable cells (e.g. non-red blood cells) are retrieved from the sample using known techniques, and optionally concentrated. Those of skill in the art are familiar with methods for concentrating such cells, including but not limited to centrifugation, concentration in a gradient (e.g. a ficol gradient), or by isolation by fluorescence activated cell sorting (FACS), or by various commercially available PBMC isolation kits (e.g. SepMate™), etc. Cells may optionally be cultured prior to testing to increase their numbers. The cells are then exposed to (e.g. incubated with) a construct comprising the mda-9/syntenin promoter operationally linked to gene encoding a reporter molecule. The reporter gene may be any suitable gene known in the art, e.g. as described herein. In one aspect, the gene is a luciferase gene, and an exemplary construct is mda-9-Prom-Luc.

The construct may be of any type described herein, so long as the construct can enter the cells in the sample. In one exemplary aspect, the construct is a nanoparticle, e.g. a PH nanoparticle construct such as mda-9-Prom-Luc-PEI. However, other constructs, including other nanoparticle constructs, may also be utilized.

The mixture of cells and construct are then treated so as to activate the reported gene as described elsewhere herein, i.e. steps are taken so that a detectable signal is generated from the expressed (transcribed and translated) reported gene, if expression has occurred. For example, if a luciferase gene is employed, luciferin is added. In some aspects, the cells are separated from the mixture of cells plus construct prior to activation of the signal. However, in some aspects, the signal is intrinsic to the reporter i.e. the translated reporter gene product is detectable without the addition of further activating substances. Expression of the reported gene occurs selectively in cancer cells, or cells that have metastatic potential, e.g. cells that are expressing factors known to be associated with cancer or the development of cancer or metastasis. Even though the construct enters normal, non-cancer cells, mda-9/syntenin is not active in such cells, the reporter gene is not produced, and substantially no signal is generated.

Following activation of the reporter gene (if required), production of the detectable signal that is generated is detected or measured. For example, the cells are viewed under a fluorescent microscope or using another suitable technique. Other suitable techniques include but are not limited to: fluorescence-activated cell sorting (FACS), enzyme-linked immunosorbent assay (ELISA) which employ antibodies, methods which measure radioactivity, chemiluminescent reporter assays (e.g. commercially available kits to detect Secreted alkaline phosphatase (SEAP) and ϵ-galactosidase and luciferase reporters), by cell sorting based on charge of size, etc. Any suitable technique may be used as long as it corresponds and it effective to detect the reporter genes that is used, which may be any of those described herein. Cells exhibiting or producing a detectable signal (e.g. showing fluorescence) would be considered cancer cells, and those with elevated expression as compared to similarly treated (control) non-metastatic and fully metastatic cancer cells would be classified as putative metastatic cells.

Figure 3:
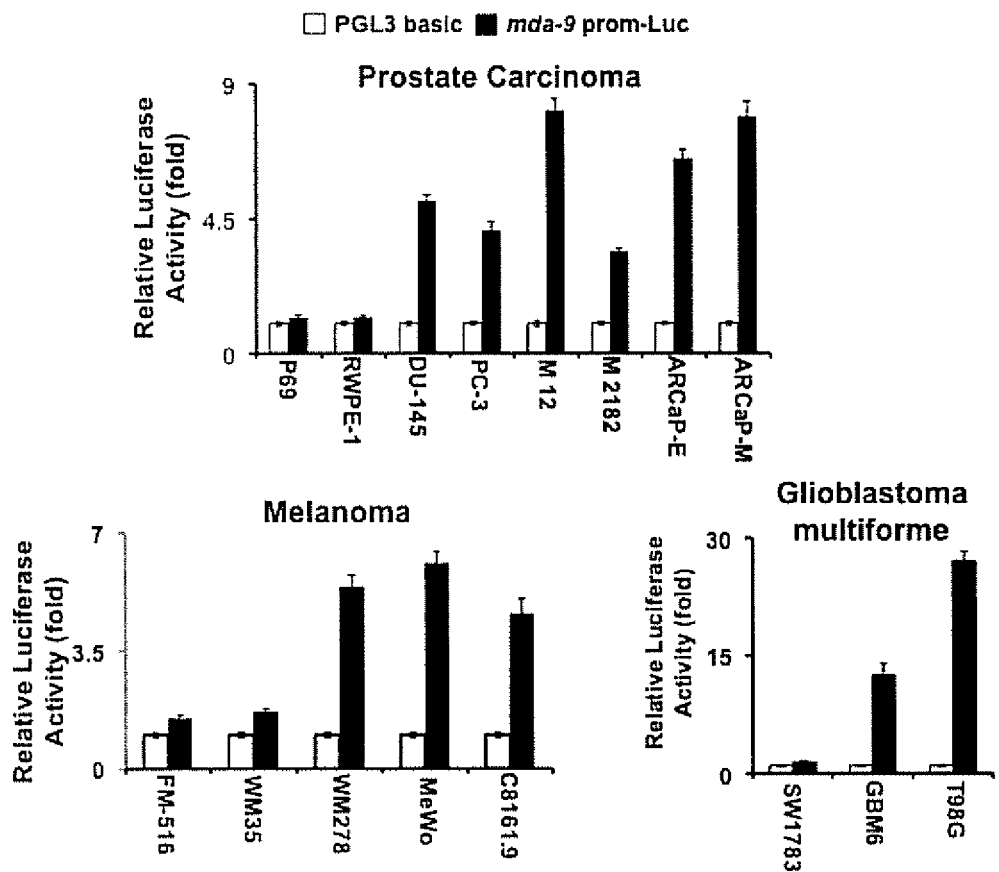
FIG. 3. mda-9 promoter activity in various cancer cells compared to normal cells.

Classification of the cells as normal, cancerous or incipient (developing) cancer cells typically involves a comparison of the signal from the cells to signals generated by suitable control cells such as cells of the same type (e.g. breast, melanoma, prostate, GBM cells, etc.) that are i) known to be normal, ii) known to be cancerous, and/or iii) known to be in the process of becoming cancerous, e.g. are pre-cancerous. For example, when using a fluorescent reporter such as luciferase and assessing prostate cancer cells, in a comparative fold scale of relative luciferase activity (RFA), normal prostate cells typically exhibit an activity of less than about 1 or 2, and prostate cancer cells exhibit a RFA of at least about 4, or greater, e.g. about 4, 5, 6, 7, 8, 9, 10 or more. For other cell types, the ranges may be greater (e.g. GBM cells exhibit about a 10-30-fold higher RFA than normal control cells, and for melanoma cells, the cancerous cells exhibit an RFA in the range of at least about 3 to about 7, e.g. 3, 4, 5, 6, 7 or more (see FIG. 3). A pre-cancerous cell would then typically exhibit a detectable signal greater than a control cell but less than a cancer cell, e.g. about 20, 25, 30, 35, 40, 45, 50, 55, 60, 65, 70 or 75% of the signal of a cancer cell. Antibodies may also be used to distinguish between cancerous and normal cells, as may cell surface antigens, etc. Suitable biological samples include but are not limited to: blood, plasma, mucous, saliva, urine, "washes" of various parts of the body (eg the oral cavity vagina, colorectal tract, tissue (e.g. homogenized tissue from biopsies or other samples), etc. Those of skill in the art will recognize that one or more steps of washing the cells in a sample, with or without concentration of the cells, may be carried out at any step of the assay, as needed e.g. to increase the signal, to remove extraneous material, to reduce noise, etc.

In addition, the invention provides kits for carrying out the rapid in vitro assay described herein. The kits typically contain a construct comprising at least one mda-9 promoter as described herein, which may be provided as a liquid or as a reconstitutable solid (e.g. lyophilized), reagents for activating the signal from the expressed reporter gene, if required, and instructions for use. Standards for calibrating the signal may also be included and/or a scale comprising cut-off values for classifying cells as cancerous, normal, or pre-cancerous, and in fact, samples of such cells may be included in the kit. The kit may include one or more containers, e.g. a packaging/shipping container, and smaller individual containers, test tubes, etc. within the package for carrying out the assay.

The following examples are provided in order to illustrate several examples of the practice of the invention, but should not be construed as limiting the invention in any way.

EXAMPLES

Example 1 mda-9 Promoter Activity is Higher in Aggressive Cancer Cells Irrespective of their Anatomic Origin The cell lines used in this study:
Prostate Cancer: The mda-9 promoter activity in different human prostate cancer cell lines (PC-3, DU-145, M 12, M 2182, ArCaP-E, ArCaP-M) were compared with two non-tumorigenic immortal human prostate epithelial cells including P69 and RWPE-1. Here, it is worthy to mention that M12 is the metastatic variant of non-tumorigenic P69 cells. In addition, mda-9 promoter activity was also compared between mesenchymal ARCaP-M (metastatic variant) cells with epithelial variants ARCaP-E.
Melanoma: Different melanoma cell lines were used in this experiment including radial growth phase melanoma WM35, vertical growth phase melanoma WM278, and metastatic melanoma cell lines MeWo, C8161.9. A clone of normal immortal human melanocytes FM516-SV (referred to as FM-516) was used to understand the differential expression of mda-9 promoter activity in metastatic melanoma.
Glioblastoma multiforme (GBM): Human malignant glioma cells GBM6, T98G and grade III astrocytoma line Sw1783 were used to analyze the mda-9 promoter activity.

Cancer lines obtained from different anatomic origins (prostate, melanoma and glioblastoma multiforme (GBM), see descriptions above) were transfected with a firefly luciferase (fLuc) expression vector driven by an ~1-kb promoter region of the human mda-9 gene along with a Renillar luciferase (rLuc) vector. The fLuc activity was normalized by rLuc activity and also by the activity of empty pGL3-basic vector. The data presented as mean±S.D and the results are presented in FIG. 3.

As can be seen, mda-9 promoter activity is elevated in all the cancer subtypes as compared to their normal counterparts, indicating cancer-selectivity of the mda-9 promoter, supporting the use of such constructs in an in vitro assay.

Example 2

Determination of the Minimal Active Promoter Region

Figure 5:
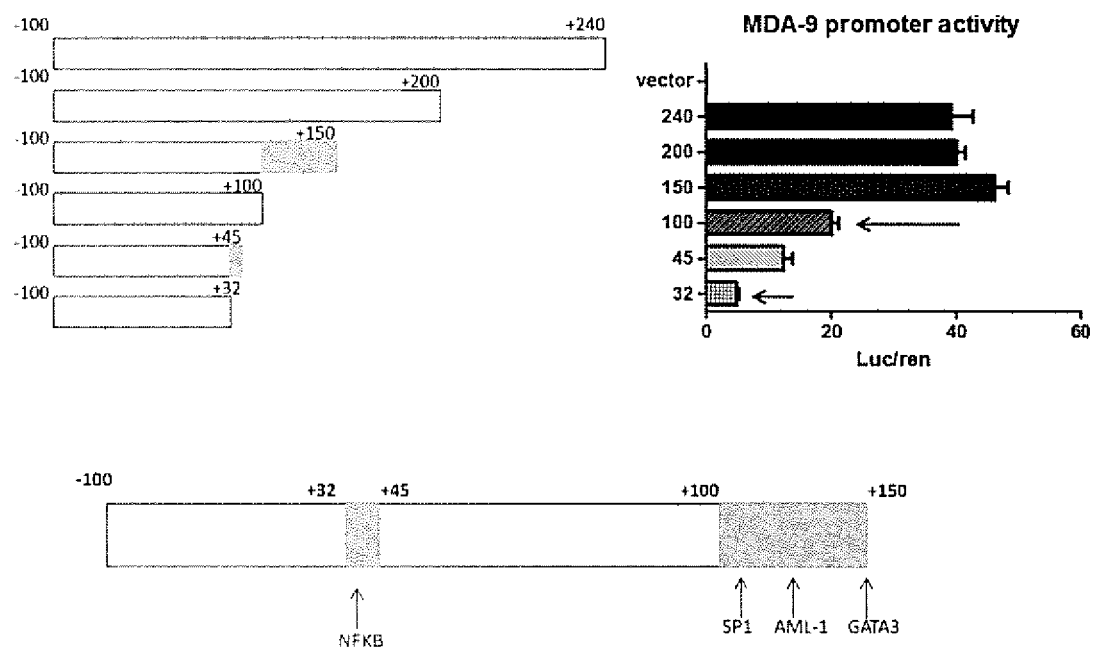
FIG. 5. 3' deletions of the mda-9 promoter were generated and the luciferase activity was determined in breast cancer cells. Numbering is with reference to the sequence in FIG. 2A.

Several 5' or 5' and 3' deletions of the mda-9 promoter were generated to determine the minimal active promoter region. The results are presented in FIGS. 4 A and B. The mda-9 promoter was found to be regulated in the first intron region (as indicated by shading in FIG. 4A). Further 3' deletions of the mda-9 promoter were generated to determine the transcription factors that regulate mda-9 expression. A small region (indicated by shading in FIG. 5) appears to regulate the mda-9 promoter. Likely transcription factor binding sites in this region are also shown in FIG. 5.

Example 3

Use of the mda-9 Promoter to Generate Vectors/Constructs for Treatment and/or Imaging of Cancer Cells, Especially Metastatic Cancer Cells Recombinant vectors are constructed in which expression of one or more genes of interest (usually only one) is operably linked to the mda-9 promoter. In some aspects, the recombinant vectors also include nucleic acids encoding one or more additional genes of interest operably linked to a promoter that is not mda-9. The genes of interest include, for example, therapeutic genes as described herein and/or imaging reporting genes as described herein and/or gene required for vector replication, etc. When administered to a host (e.g. a cancer patient), the vectors express the genes of interest selectively in cancer cells, especially in metastatic cancer cells, permitting visualization (imaging) and hence locating of the cells, and killing of the cells. Alternatively, the vectors are used to create transgenic mice that contain and express the proteins encoded by the vector. The mice are used to monitor tumor development and metastasis, and to screen agents that are candidates for preventing, treating or causing cancer and/or metastases.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Azab B M, Dash R, Das S K, Bhutia S K, Sarkar S, Shen X N, Quinn B A, Dent P, Dmitriev I P, Wang X Y, Curiel D T, Pellecchia M, Reed J C, Sarkar D, Fisher P B. Enhanced prostate cancer gene transfer and therapy using a novel serotype chimera cancer terminator virus (Ad.5/3-CTV). J Cell Physiol. 2014; 229(1): 34-43.

Azab B, Dash R, Das S K, Bhutia S K, Shen X N, Quinn B A, Sarkar S, Wang X Y, Hedvat M, Dmitriev I P, Curiel D T, Grant S, Dent P, Reed J C, Pellecchia M, Sarkar D, Fisher P B. Enhanced delivery of mda-7/IL-24 using a serotype chimeric adenovirus (Ad.5/3) in combination with the Apogossypol derivative BI-97C1 (Sabutoclax) improves therapeutic efficacy in low CAR colorectal cancer cells. J Cell Physiol. 2012; 227(5): 2145-2153.

Bhang H E, Gabrielson K L, Laterra J, Fisher P B, Pomper M G. Tumor-specific imaging through progression elevated gene-3 promoter-driven gene expression. Nat Med. 2011; 17:123-129.

Bonnet M E, Erbacher P, Bolcato-Bellemin A L. Systemic delivery of DNA or siRNA mediated by linear polyethylenimine (L-PEI) does not induce an inflammatory response. Pharm Res. 2008; 25: 2972-2982.

Boukerche H, Aissaoui H, Prvost C, Hirbec H, Das S K, Su Z, Sarkar D, Fisher P B. Src kinase activation is mandatory for MDA-9/syntenin-mediated activation of nuclear factor-kappaB. Oncogene. 2010; 29: 3054-3066.

Boukerche H, Su Z Z, Emdad L, Baril P, Balme B, Thomas L, Randolph A, Valerie K, Sarkar D, Fisher P B. mda-9/Syntenin: a positive regulator of melanoma metastasis. Cancer Res. 2005; 65: 10901-10911.

Boukerche H, Su Z, Prvot C, Sarkar D, Fisher P B. 2008. mda-9/Syntenin promotes metastasis in human melanoma cells by activating c-Src. Proc Natl Acad Sci USA. 2008; 105: 15914-15919.

Das S K, Bhutia S K, Azab B, Kegelman T P, Peachy L, Santhekadur P K, Dasgupta S, Dash R, Dent P, Grant S, Emdad L, Pellecchia M, Sarkar D, Fisher P B. MDA-9/Syntenin and IGFBP-2 Promote Angiogenesis in Human Melanoma. Cancer Res. 2013; 73(2): 844-854.

Das S, Bhutia S, Kegelman T, Peachy L, Oyesanya R, Dasgupta S, Sokhi U, Azab B, Dash R, Quinn B, Kim K, Barral P, Su Z, Boukerche H, Sarkar D, Fisher P B. MDA-9/syntenin: a positive gatekeeper of melanoma metastasis. Frontiers in Bioscience. 2012a; 17: 1-15.

Das S K, Sarkar S, Dash R, Dent P, Wang X Y, Sarkar D, Fisher P B. Cancer terminator viruses and approaches for enhancing therapeutic outcomes. Adv. Cancer Res. 2012b: 115: 1-38.

Dash R, Azab B, Quinn B A, Shen X, Wang X Y, Das S K, Rahmani M, Wei J, Hedvat M, Dent P, Dmitriev I P, Curiel D T, Grant S, Wu B, Stebbins J L, Pellecchia M, Reed J C, Sarkar D, Fisher P B. Apogossypol derivative BI-97C1 (Sabutoclax) targeting Mcl-1 sensitizes prostate cancer cells to mda-7/IL-24-mediated toxicity. Proc Natl Acad Sci USA. 2011a; 108(21): 8785-8790.

Dash R, Azab B, Shen X N, Sokhi U K, Sarkar S, Su Z Z, Wang X Y, Claudio P P, Dent P, Dmitriev I P, Curiel D T, Grant S, Sarkar D, Fisher P B. Developing an effective gene therapy for prostate cancer: New technologies with potential to translate from the laboratory into the clinic. Discov Med. 2011b; 11(56): 46-56.

Dash R, Dmitriev I, Su Z Z, Bhutia S K, Azab B, Vozhilla N, Yacoub A, Dent P, Curiel D T, Sarkar D, Fisher P B. Enhanced delivery of mda-7/IL-24 using a serotype chimeric adenovirus (Ad.5/3) improves therapeutic efficacy in low CAR prostate cancer cells. Cancer Gene Ther. 2010; 17(7): 447-456.

Fisher P B. Is mda-7/IL-24 a "magic bullet" for cancer? Cancer Res. 2005; 65(22): 10128-10138.

Greco A, Di Benedetto A, Howard C M, Kelly S, Nande R, Dementieva Y, Miranda M, Brunetti A, Salvatore M, Claudio L, Sarkar D, Dent P, Curiel D T, Fisher P B, Claudio P P. Eradication of therapy-resistant human prostate tumors using an ultrasound-guided site-specific cancer terminator virus delivery approach. Mol Ther. 2010; 18(2):295-306.

Grootjans J J, Zimmermann P, Reekmans G, Smets A, Degeest G, Drr J, David G. Syntenin, a PDZ protein that binds syndecan cytoplasmic domains. Proc Natl Acad Sci USA. 1997; 94:13683-13688.

Jiang H, Fisher P B. Use of a sensitive and efficient subtraction hybridization protocol for the identification of genes differentially regulated during the induction of differentiation in human melanoma cells. Mol Cell Different. 1993; 1: 285-299.

Jiang H, Su Z Z, Lin J J, Goldstein N I, Young C S, Fisher P B. The melanoma differentiation associated gene mda-7 suppresses cancer cell growth. Proc Natl Acad Sci USA. 1996; 93(17): 9160-9165.

Kegelman T P, Das S K, Flu B, Bacolod M D, Fuller C E, Menezes M E, Emdad L, Dasgupta S, Baldwin A S, Bruce J N, Dent P, Pellecchia M, Sarkar D, Fisher P B. MDA-9/syntenin is a key regulator of glioma pathogenesis. Neuro Oncol. 2014; 16: 50-61.

Lin J, Jiang H, Fisher P. Characterization of a novel melanoma differentiation-associated gene, mda-9, that is down-regulated during terminal cell differentiation. Mol Cell Differ. 1996; 4: 317-333.

Lin, J. J., H. Jiang and P. B. Fisher. Melanoma differentiation associated gene-9 is a human gamma interferon responsive gene. Gene 1998; 207: 105-110.

Qian X, Li Y, Yu B, Gu F, Liu F, Li W, Zhang X, Fu L. Syndecan Binding Protein (SDCBP) Is Overexpressed in Estrogen Receptor Negative Breast Cancers, and Is a Potential Promoter for Tumor Proliferation. Plos One. 2013; 8:e60046.

Sarkar S, Azab B, Quinn B A, Shen X, Dent P, Klibanov A L, Emdad L, Das S K, Sarkar D, Fisher P B. Chemoprevention gene therapy (COT) of pancreatic cancer using perillyl alcohol and a novel chimeric serotype cancer terminator virus. Curr Mol Med. 2014; 14(1):125-140.

Sarkar D, Boukerche H, Su Z Z, Fisher P B. Mda-9/syntenin: Recent Insights into a Novel Cell Signaling and Metastasis-Associated Gene. Pharmacal Ther. 2004; 104:101-115.

Sarkar D, Lebedeva I V, Su Z Z, Park E S, Chatman L, Vozhilla N, Dent P, Curiel D T, Fisher P B. Eradication of therapy-resistant human prostate tumors using a cancer terminator virus. Cancer Res. 2007; 67: 5434-5442.

Sarkar D, Su Z Z, Vozhilla N, Park E S, Gupta P, Fisher P B. Dual cancer-specific targeting strategy cures primary and distant breast carcinomas in nude mice. Proc Natl Acad Sci USA. 2005a; 102: 14034-14039.

Sarkar D, Su Z Z, Vozhilla N, Park E S, Randolph A, Valerie K, Fisher P B. Targeted virus replication plus immunotherapy eradicates primary and distant pancreatic tumors in nude mice. Cancer Res. 2005b; 65: 9056-9063.

Su Z Z, Goldstein N I, Jiang H, Wang M N, Duigou G J, Young C S, Fisher P B. PEG-3, a nontransforming cancer progression gene, is a positive regulator of cancer aggressiveness and angiogenesis. Proc Natl Acad Sci USA. 1999; 96: 15115-15120.

Su Z Z, Sarkar D, Emdad L, Duigou G J, Young C S, Ware J, Randolph A, Valerie K, Fisher P B. Targeting gene expression selectively in cancer cells by using the progression-elevated gene-3 promoter. Proc Natl Acad Sci USA. 2005; 102: 1059-1064.

We claim:

1. A recombinant vector comprising a mda-9 cancer selective promoter comprising the sequence set forth in SEQ ID NO: 2, wherein said recombinant vector is a viral vector.

2. The recombinant vector of claim 1, wherein said mda-9 cancer selective promoter is operably linked to at least one gene of interest.

3. The recombinant vector of claim 1, wherein said viral vector is selected from the group consisting of: an adenoviral vector, a lentiviral vector, a herpes simplex virus, a measles virus, and a vaccinia virus.

4. The recombinant vector of claim 1, wherein said recombinant vector is present in a nanoparticle carrier.

5. The recombinant vector of claim 4, wherein said nanoparticle carrier comprises polyethyleneimine (PEI).

6. The recombinant vector of claim 2, wherein said at least one gene of interest encodes one or more of an anticancer agent, an imaging agent, and at least one gene that is required for viral replication.

7. The recombinant vector of claim 1, wherein said mda-9 cancer selective promoter comprises the sequence set forth in SEQ ID NO: 1.

8. A mammalian cell comprising the recombinant vector of claim 1.

9. The mammalian cell of claim 8, wherein said cell is a cancer cell.

10. A method of treating cancer and/or metastatic cancer in a patient in need thereof, comprising administering to said patient a composition comprising the recombinant vector of claim 6, wherein said at least one gene of interest encodes an anticancer agent.

11. The method of claim 10, wherein said cancer is selected from the group consisting of melanoma, brain cancer, breast cancer, liver cancer, esophageal cancer, cervical cancer, lung cancer, colon cancer, bladder cancer, uterine cancer, endometrial cancer, gastric cancer, pancreatic cancer, prostate cancer, neuroblastoma, sarcoma, and thyroid cancer.

12. The method of claim 10, wherein said cancer is metastatic cancer.

13. An in vitro method for detecting cancerous and pre-cancerous cells in a biological sample from a patient, comprising administering to cells in said biological sample the recombinant vector of claim 6, wherein said at least one gene of interest encodes an imaging agent.

14. The in vitro method of claim 13, wherein said biological sample is blood.

15. The in vitro method of claim 13, wherein said recombinant vector is formulated for administration as a nanoparticle.

16. The in vitro method of claim 15, wherein said nanoparticle comprises polyethyleneimine (PEI).

17. The recombinant vector of claim 6, wherein the recombinant vector is a viral vector, and wherein the vector, in addition to the mda-9 cancer selective promoter, comprises a second promoter operably linked to a gene encoding one or more of an anticancer agent, an imaging agent, and a gene required for viral replication.

18. The recombinant vector of claim 17, wherein the vector comprises a third promoter operably linked to a gene encoding one or more of an anticancer agent, an imaging agent, and a gene required for viral replication; wherein the recombinant vector comprises at least one each of the anticancer agent, the imaging agent, and the gene required for viral replication.

19. The recombinant vector of claim 18, wherein the anticancer agent is operably linked to the mda-9 cancer selective promoter.

20. A recombinant vector comprising a mda-9 cancer selective promoter comprising the sequence set forth in SEQ ID NO: 2, wherein said recombinant vector is a plasmid vector, wherein said mda-9 cancer selective promoter is operably linked to at least one gene of interest, and wherein said at least one gene of interest encodes one or more of an anticancer agent, an imaging agent.

21. The recombinant vector of claim 20, wherein said recombinant vector is present in a nanoparticle carrier.

22. The recombinant vector of claim 21, wherein said nanoparticle carrier comprises polyethyleneimine (PEI).

23. The recombinant vector of claim 20, wherein said mda-9 cancer selective promoter comprises the sequence set forth in SEQ ID NO: 1.

24. The recombinant vector of claim 20, wherein the vector, in addition to the mda-9 cancer selective promoter, comprises a second promoter operably linked to a gene encoding one or more of an anticancer agent and an imaging agent.

25. The recombinant vector of claim 24, wherein the vector comprises a third promoter operably linked to a gene encoding one or more of an anticancer agent and an imaging agent.

26. The recombinant vector of claim 25, wherein the anticancer agent is operably linked to the mda-9 cancer selective promoter.

* * * * *